United States Patent
Balu et al.

(10) Patent No.: US 7,482,433 B2
(45) Date of Patent: Jan. 27, 2009

(54) PEPTIDES AND COMPOUNDS THAT BIND TO THE IL-5 RECEPTOR

(75) Inventors: Palani Balu, Cupertino, CA (US); Qun Yin, Palo Alto, CA (US); Bruce England, Hayward, CA (US)

(73) Assignee: Affymax, Inc., Palo Alto, CA (US)

( * ) Notice: Subject to any disclaimer, the term of this patent is extended or adjusted under 35 U.S.C. 154(b) by 173 days.

(21) Appl. No.: 11/381,172

(22) Filed: May 2, 2006

(65) Prior Publication Data

US 2007/0173444 A1 Jul. 26, 2007

Related U.S. Application Data

(62) Division of application No. 10/168,372, filed as application No. PCT/US99/30081 on Dec. 16, 1999, now Pat. No. 7,109,299.

(51) Int. Cl.
*A61K 38/00* (2006.01)
*A61K 45/00* (2006.01)
*C07K 17/00* (2006.01)

(52) U.S. Cl. .............. 530/351; 530/324; 530/326; 530/327; 530/388.2; 530/402; 424/85.2; 514/2; 514/12; 514/13; 514/14

(58) Field of Classification Search .......... 530/351, 530/324, 326, 327, 388.2, 402; 424/85.2; 514/12, 13, 14
See application file for complete search history.

(56) References Cited

U.S. PATENT DOCUMENTS

| 3,645,090 A | 2/1972 | Mochizuki et al. |
|---|---|---|
| 3,940,475 A | 2/1976 | Gross |
| 4,179,337 A | 12/1979 | Davis et al. |
| 4,301,144 A | 11/1981 | Iwashita et al. |
| 4,496,689 A | 1/1985 | Mitra |
| 4,612,132 A | 9/1986 | Wollenberg et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 5,096,704 A | 3/1992 | Coffman et al. |
| 5,126,352 A | 6/1992 | Ganguly et al. |
| 5,143,854 A | 9/1992 | Pirrung et al. |
| 5,270,170 A | 12/1993 | Schatz et al. |
| 5,338,665 A | 8/1994 | Schatz et al. |

(Continued)

FOREIGN PATENT DOCUMENTS

CA 2058003 12/1991

(Continued)

OTHER PUBLICATIONS

U.S. Appl. No. 07/624,120, filed Dec. 6, 1990, Fodor, et al.

(Continued)

*Primary Examiner*—Jon Weber
*Assistant Examiner*—Abdel A Mohamed
(74) *Attorney, Agent, or Firm*—Goodwin Procter LLP

(57) ABSTRACT

Interleukin-5 receptor (IL-5R) ligands comprising amino sequences of formula TGGGDGYVX$_3$VEX$_4$ARCPTCK, EGYVX$_3$VEX$_4$ARCPTCK, EGYVX$_3$VEX$_4$ARCPTCR, GYVX$_3$VEX$_4$ARCPTCG, EGYVX$_3$VEX$_4$ARCPTCG, GYVX$_3$VEX$_4$ARCPTCR, and EGYVX$_3$VEX$_4$AACPTCR, and methods of using the same, are described and claimed.

14 Claims, 5 Drawing Sheets

U.S. PATENT DOCUMENTS

| | | | |
|---|---|---|---|
| 5,359,115 | A | 10/1994 | Campbell et al. |
| 5,420,328 | A | 5/1995 | Campbell et al. |
| 5,424,186 | A | 6/1995 | Fodor et al. |
| 5,432,018 | A | 7/1995 | Dower et al. |
| 5,580,751 | A | 12/1996 | Buchardt et al. |
| 5,654,276 | A | 8/1997 | Barrett et al. |
| 5,668,110 | A | 9/1997 | Barrett et al. |
| 5,677,280 | A | 10/1997 | Barrett et al. |
| 5,683,983 | A | 11/1997 | Barrett et al. |
| 5,770,358 | A | 6/1998 | Dower et al. |
| 5,846,933 | A | 12/1998 | Korngold et al. |
| 6,268,471 | B1 | 7/2001 | Romeo |
| 7,109,299 | B1 * | 9/2006 | Balu et al. .................. 530/351 |

FOREIGN PATENT DOCUMENTS

| | | |
|---|---|---|
| CA | 2078384 | 9/1992 |
| EP | 45665 | 9/1985 |
| EP | 0 533 066 A1 | 3/1997 |
| EP | 475746 | 7/2000 |
| GB | 9712410.1 | 6/1997 |
| WO | WO 90/15070 | 12/1990 |
| WO | WO 90/16184 | 8/1993 |
| WO | WO 94/28170 | 12/1994 |
| WO | WO 95/14040 | 5/1995 |
| WO | WO 95/34326 | 12/1995 |
| WO | WO 98/57979 | 12/1998 |
| WO | WO 98/57991 | 12/1998 |

OTHER PUBLICATIONS

U.S. Appl. No. 07/847,567.
U.S. Appl. No. 07/947,339, filed Sep,. 18, 1992.
U.S. Appl. No. 08/081,577, filed Jun. 21, 1993, Campbell, et al.
U.S. Appl. No. 08/147,805.
U.S. Appl. No. 10/168,372.
Akaji, et al., Regioselective Double Disulfide Formation using Silylchloride-Sulfoxide system Tetrahedron Letters, vol. 33, 1073-1076, (1992).
Almquist, et al., Synthesis and Biological Activity of a Ketomethylene Analogue of a Tripeptide Inhibitor of Angiotensin Converting Enzyme, J. Med. Chem., vol. 23, 1392-1398, (1980).
Barker, et al., Cyclic RGD Peptide Analogues as Antiplatelet Antithrombotics, J. Med. Chem., vol. 35, No. 11, (1992).
Bodonszky, et al., Communications to the editor, Chem. Ind., vol. 38, 1597-1598, (1966).
Bundgaard, et al., Design of Prodrugs, Elsevier Science Publishers, (1985).
Caras, et al., Signal Peptide Secretion Directing Glycophospholipid Membrane anchor Attachment, Science, vol. 243, No. 4895, 1196-1198, (1989).
Chan et al., A 3-Amino-4-hydroxy-3-cyclobutene-1,2-dione-containing Glutamate Analogue Exhibiting high Affinity to Excitatory amino Acid Receptors, J. Med. Chem., vol. 38, No. 22, 4433-4438, (1995).
Chiu, et al., Gastric Cytoprotective Properties of SCH 32651, A Novel Antiulcer Agent, Arch. Int. de Pharm. et de Thera, vol. 270, 128-140, (1984).
Cho, et al., An Unnatural Biopolymer, Science, vol. 261, No. 5126, 1303-1305, (1993).
Cwirla, et al., Peptides on phage: A Vast Library of peptides for identifying ligands, Proc. Natl. Acad. Sci., vol. 87, 6378-6382, (1990).
Delgado, et al., The Uses and Properties of PEG-Linked Proteins, Critical Reviews in therapeutic drug carrier system, vol. 9, 249-304, (1992).
Devos, R. et al., Interleukin-5 and its receptor: A drug target for Eosinophilia associated with chronic allergic disease, Journal of Leukocyte Biology, vol. 57, 813-819, (1995).
Devos, R. et al., Recombinant soluble human interleukin-5 (hIL-5) receptor molecules, J. of Biol. Chem., vol. 268, No. 9, 6581-6587, (1993).
Dower, et al., The search for molecular diversity (2): recombinant and synthetic randomized peptide libraries, Ann. Rep. Med. Chem., vol. 26, Ch. 28, 271-280, (1991).
England, et al., A potent dimeric peptide antagonist of interleukin-5 that binds two interleukin-5 receptor a chains, PNAS, /vol. 97, No. 12, 6862-6867, (2000).
Evans, et al., Design of Nonpeptidal ligands for a Peptide receptor: Cholecystokinin Antagonists, J. Med. Chem., vol. 30, 1229-1239, (1987).
Fattah, D., et al., A rapid activation assay for human eosinophils based on adhesion to immobilized ICAM-1, VCAM-1 and IgG, Cytokine, vol. 8, No. 3, 248-259, (1996).
Fauchere, Elements for the rational design of peptide drugs, J. Adv. Drug Res., vol. 15, 29-69, (1986).
Fodor, et al., Light-Directed, spatially addressable parallel chemical synthesis, Science, vol. 251, No. 4995, 767-773, (1991).
Ganderton, et al., Drug Delivery to the respiratory tract, Book (1987), Ellis Horwood, England.
Gilman, et al., Goodman and Gilman's: The Pharmacological Basis of Therapeutics, 8$^{th}$ Ed, (1990).
Gisin, Helv. Chim. Acta., vol. 56, 1467, (1973).
Gonda, Aerosols for delivery of therapeutic and diagnostics agents to the respiratory tract, Critical reviews in therapeutic drug carrier systems, vol. 6, 373-313, vol. 6, Issue 4, (1990).
Hann, et al., On the double bond isostere of the peptide bond: Preparation of an enkephalin Analogue, J. Chem. Soc. Perkin Trans., The Royal Society of Chemistry, 307-314, (1982).
Hayashida, Molecular cloning of a second subunit of the receptor for human granulocyte-macrophage colony-stimulating factor (GM-CSF): Reconstitution of a high-affinity GM-CSF receptor, Proc. Natl. Acad. Sci., vol. 87, 9655-9659, (1990).
Holladay, et al., Synthesis of Hydroxyethylene and ketomethyleve dipeptide isosteres, Tetrahedron Letters, vol. 24, No. 41, 4401-4404, (1983).
Honek, J., Unnatural Amino Acids, http://www.science.uwaterloo.ca/~jhonek/UnnaturalAA.html.
Hruby, Conformational restrictions of biologically active peptides via amino acids side chain groups, Life Sci., vol. 31, No. 3, 189-199, (1982).
Hruby, et al., Emerging approaches in the molecular design of receptor-selective peptide ligands: conformational, topographical and dynamic consideration, Biochem. J., vol. 268, 249-262, (1990).
Hudson, et al., Methionine Enkaphalin and isosteric analogues, Int. J. Pept. Prot. Res., vol. 14, 177-185, (1979).
Jennings-White, et al., Synthesis of ketomethylene analogs of dipeptudes, Tetrahedron Letters, vol. 23, No. 25, 2533-2534, (1982).
Johanson, et al., Binding interaction of human interleukin 5 with its receptors a subunit, J. Biol. Chem., vol. 270, No. 16, 9459-9471, (1995).
Larson, Experimental models of reversible airway obstruction, The lung: Scientific Foundations, (1991).
Lin, et al., Expression of T cell antigen receptor heterodimers in a liquid-linked form. Science, vol. 249, No. 4969, 677-679, (1990).
Lopez, et al., Recombinant human interleukin 5 is a selective activator of human eosinophil funcation, J. Exp. Med., vol. 167, 219-224, (1988).
March, Advanced organic chemistry, John Wiley & Sons. 3$^{rd}$ ed., 1052-1061, (1985).
Mark, et al., Encyclopedia of chemical technology book, John Wiley & Sons, vol. 1-24, 3$^{rd}$ Edition, (1980).
Martens, et al., A Generic particle-based nonradioactive homogeneous multiplex method for high-throughput screening using microvolume fluorimetry, Anal. Biochem., vol. 273, 20-31, (1999).
Mckinnon, et al., An Interleukin 5 mutant distinguishes between two functional responses in human eosinophils, J. Exp. Med., vol. 186, No. 1 (1997).
Merrifield, Solid Phase peptide synthesis. I. The synthesis of a tetrapeptide, J. am. chem.. Soc., vol. 85, 2149-2154, (1963).
Minamitake, Y., et al., Structure of recombinant human interleukin-5 produced by Chinese hamster ovary cells, Journal of Biochemistry, vol. 107, No. 2, 292-297, (1990).

Monfardini, et al., A branched monomethoxpoly (ethylene glycol) for protein modification, bioconjugate Chem., vol. 6, No. 1, 62-69, (1995).

Moroder, et al., Oxidative folding of cystine-rich peptides vs. regioselective Cysteine pairing strategies, vol. 40, 207-234, (1996).

Morgan, et al., Approaches to the discovery of non-peptide ligands for peptide receptors and peptidases, Ann. rep. Med. Chem., vol. 24, ch. 26, 243-252, (1989).

Murata, et al., Molecular cloning and expression of the human interleukin 5 receptor, J. exp. Med., vol. 175, 341-351, (1992).

Or, et al., Cysteine Alkylation in unprotected peptides: Synthesis of a carbavasopressin analogue by intramolecular Cysteine alkylation, J. Org. Chem., vol. 56, No. 9, 3146-3149, (1991).

Pietta, et al., Amide protection 1 and Amide supports in solid-phase peptide synthesis, Chem.. Comm., vol. 485, 650-651, (1970).

Plaetinck, et al., Characterization of interleukin 5 receptor on eosinophilic sublines form human promyelocytic leukemia (HL-60) Cells, J. Exp. Med., vol. 172, 683-691, (1990).

Portanova, et al., Rapid and selevtive induction of blood eosinophilia in guinea pigs by recombinant human interleukin 5, Cytokine, vol. 7, No. 8, 775-783, (1995).

Raeburn, et al., Techniques for drug delivery to the airways, and the assessment of lung function in animal models, J. Pharmacol. Toxical. Methods, vol. 27, No. 3, 143-159, (1992).

Rizo, et al., Contained peptides models of bioactive peptides and protein substructures, Ann. Rev. Biochem., vol. 61, 387-418, (1992).

Rolink, et al., Monoclonal antibodies reactive with the mouse interleukins 5 receptor, J. Exp. Med., vol. 169, 1693-1701, (1989).

Saito, et al., Selective differentiation and proliferation of hematopoietic cells induced by recombinant human interleukins, Proc. Natl. Acad. Sci., vol. 85, 2288-2292, (1988).

Schstz, P., Use of peptide libraries to map the substrate specificity of a peptide-modifying enzyme: A thirteen residue consensus peptide specifies biotinylation in *Escherischia coli*, Biotechnology, vol. 11, 1138-1143, (1993).

Spatola, A. F., et al., Structure-Activity relationships of enkephalins containing serially replaced thiomethylene amide bond surrogates, Life Sci., vol. 38. No. 14, 1243-1249, (1986).

Stewart, et al., Solid phase peptide synthesis, Freeman and Co., (1969).

Stewart and Young, Solid phase peptide synthesis, $2^{nd}$ edition, Pierce chemical, (1984).

Tam, J.P., et al., Disulfide Bond formation in peptides by dimethyl sulfoxide, scope and applications, j. Am. Chem. Soc., vol. 113, No. 17, 6657-6662, (1991).

Tamamura, et al., Unambiguous synthesis of stromal cell-derived factor-1 by regioselective disulfide bond formation using a DMSO-aqueous HCL system, Chem. Commun., vol. 1, 151-152, (1998).

Uings, et al., Development of IL-5 receptor antagonists, current pharmaceutical design, vol. 8, 1837-1844, (2002).

Uings, et al., Modified peptide antagonists interleukin-5 exhibit extended in vivo persistence but restricted species specificity, Cytokine, vol. 15, No. 1, 10-19, (2001).

Verber, et al., The design of metabolically-stable peptide analogs, TINS, 392-396, (1985).

Wanner, et al., Models of airway hyperresponiveness, Am. Rev. Respir. dis., vol. 141, 253-257, (1990).

Whitehorn, e.A., et al., A generic method for expression and use of Tagged soluble versions of cell surface receptor, biotechnology, vol. 13, 1215-1219, (1995).

Yamaguchi, et al., Purified Interleukin 5 supports the terminal differentiation and proliferation of murine eosinophilic precursors, j. Exp. Med., vol. 167, 43-56, (1988).

Zalipsky, Functionalized poly (ethylene glycol) for preparation of biologically relevant conjugates, Bioconjugate Chem., vol. 6, No. 2, 150-165, (1995).

"Cross-linking: Homobifunctional cross-linkers", Pierce chemical Technical Library, http://www.perbio.com.cn/PIERCE/Technique/crosslink/homocros.pdf.

EMD Biosciences, Inc. Homepage, http://www.emdbiosciences.com/products/browseproductsbycategory.asp?catid=1004. (2005).

Encyclopedia of amino acid analogs and chiral building blocks 2003-2004, peptech corp., http://www.peptechcorp.com/documents/peptech2003_2004.pdf.

Remington's pharmaceutical sciences, $7^{th}$ ed., Mack Publishing Co., Easton, Penn. (1985).

\* cited by examiner

PEPTIDES AND COMPOUNDS THAT BIND TO THE IL-5 RECEPTOR

CROSS-REFERENCE TO RELATED APPLICATIONS

This application is a divisional of U.S. Ser. No. 10/168,372, filed Mar. 24, 2003, now U.S. Pat. No. 7,109,299, which is a national phasc application under 35 U.S.C. § 371 of International Application No. PCT/US99/30081, filed Dec. 16, 1999, all of which are hereby incorporated by reference in their entirety.

TECHNICAL FIELD

The present invention provides peptides and compounds that bind the interleukin 5 receptors (IL-5R), methods for assaying interleukin 5 (IL-5), and methods for inhibiting the binding of IL-5 to the IL-5R. The invention has application in the fields of biochemistry and medicinal chemistry and particularly provides IL-5 antagonists for use in the treatment of human disease.

BACKGROUND ART

Interleukin-5 (IL-5 or IL5) is a lymphokine secreted by T cells and mast cells having biological activities on B cells and eosinophils. In murine hematopoiesis, IL-5 is a selective signal for the proliferation and differentiation of the eosinophilic lineage. See Yamaguchi et al., J. Exp. Med. 167: 43-56 (1988). In this respect, IL-5 function shows analogies with colony-stimulating factors for other myeloid lineages. Also, human (h) IL-5 is very potent in the activation of human eosinophils. See Lopez et al., J. Exp. Med. 167: 219-224 (1988) and Saito et al., Proc. Natl. Acad. Sci. USA 85: 2288-2292 (1988).

IL-5 mediates its activity through a cell membrane receptor-complex. This complex has been characterized physicochemically in both the murine and human system. Mouse pre-B cell lines depending on IL-5 for their growth have been developed from bone marrow and are used for IL-5 receptor analysis. See Rolink et al., J. Exp. Med. 169: 1693-1701 (1989). The human IL-5 receptor can be studied on a subclone of the promyelocytic cell line HL60 induced towards eosinophil differentiation. See Plaetinck et al., J. Exp. Med. 172: 683-691 (1990).

Eosinophilic differentiation is initiated using sodium butyrate. Only high affinity (Kd=30 pM) IL-5 binding sites can be found on these cells. However, cross-linking studies reveal the presence of two polypeptide chains involved in IL-5 binding, i. e., IL-5R-a and IL-5R-P chains. Devos et al., Canadian Patent Publication 2,058,003 describes a recombinant a chain of human IL-5R or parts thereof, DNA-sequences coding for such a receptor or parts thereof, and host cells transformed with such vectors. Takatsu et al., European Patent Publication 475,746 provides an isolated cDNA sequence coding for murine and human IL-5 receptor. The extracellular domain (ECD) of the human IL-5R-a chain can be expressed in cells, such as CHO cells, in a manner that allows for the enzymatic harvest of the receptor from the cell surface and its subsequent immobilization using a capture antibody (E. A. Whitehorn, et al., BiolTechnology 13: 1215 (1995).

A soluble human IL-5R-a chain can be used as an IL-5 antagonist in chronic asthma or other disease states with demonstrated eosinophilia. Eosinophils are white blood cells of the granulocytic lineage. Their normal function appears to be combating parasitic infections, particularly helminthis infections. However, their accumulation in tissues, a condition referred to as eosinophilia, is also associated with several disease states, most notably asthma. It is believed that the damage to the epithelial lining of the bronchial passages in severe asthmatic attacks is largely caused by the compounds released by degranulating eosinophils.

In U.S. Pat. No. 5,096,704, there is specifically disclosed the use of compounds which block the stimulatory effects of IL-5 in order to inhibit production and accumulation of eosinophils. The stimulatory effects of IL-5 were blocked by administering an effective amount of an antagonist to human interleukin-5, preferably using monoclonal antibodies or binding compositions derived therefrom by standard techniques. Monoclonal antibodies were selected by their ability to inhibit IL-5 induced effects in standard IL-5 bioassays, such as the ability to stimulate the growth and development of eosinophils in in vitro colony forming assays, and the ability to augment in vitro proliferation of the in vivo passaged BCL 1 lymphoma cells. The use of antibody fragments, e. g., Fab fragments, was also reported.

U.S. Pat. Nos. 5,668,110; 5,677,280; 5,654,276, and 5,683,983 also discuss peptides that bind the IL-5 receptors and block the effect of IL-5.

Currently glucocorticoid steroids are the most effective drugs for treating the acute effects of allergic diseases, such as asthma. However, the availability of alternative or complementary approaches to the treatment of disorders associated with eosinophilia would have important clinical utility.

Asthma has become the most common chronic disease in industrialized countries. Conventional methods and therapeutic agents may not be completely effective in the treatment of asthma or other immunomediated inflammatory diseases in all patient populations. Moreover, there remains a need for compounds that bind to or otherwise interact with the IL-5R, both for studies of the important biological activities mediated by this receptor and for treatment of disease. The present invention provides such compounds.

DISCLOSURE OF THE INVENTION

This invention is directed, in part, to the novel and unexpected discovery that defined low molecular weight peptides and peptide mimetics have strong binding properties to the IL-5 R. The peptides are fourteen to fifty or more amino acid residues in length, preferably fourteen to twenty amino acid residues in length, and comprise a core sequence of amino acids selected from the following:

$X_1$-TGGGDGYV$X_3$VEX4ARCPTCK-$X_2$;
(residues 32-50 of SEQ ID NO:1)

$X_1$-EGYV$X_3$VE$X_4$ARCPTCK-$X_2$;
(residues 36-50 of SEQ ID NO:2)

$X_1$-EGYV$X_3$VE$X_4$ARCPTCR-$X_2$;
(residues 36-50 of SEQ ID NO:3)

$X_1$-GYV$X_3$VE$X_4$ARCPTCG-$X_2$;
(residues 36-50 of SEQ ID NO:4)

$X_1$-EGYV$X_3$VE$X_4$ARCPTCG-$X_2$;
(residues 36-50 of SEQ ID NO:5)

$X_1$-GYV$X_3$VE$X_4$ARCPTCR-$X_2$;
(residues 37-50 of SEQ ID NO:6)

and

```
            -continued
         X₁-EGYVX₃VEX₄AACPTCR-X₂
         (residues 36-50 of SEQ ID NO:7)
``` wherein X₁ is hydrogen or acyl; X₂ is —NH₂ or —OH wherein —NH₂ indicates that the carboxy terminus of the compound has been amidated and —OH indicates that the carboxy terminus of the compounds has not been derivatized; X₃ is Cys, Lys, or Dpr wherein Dpr is diaminopropionic acid, and X₄ is Nal (where Nal is 1-naphthylalanine), Trp, or Phe.

Particularly preferred compounds include the following:

```
         (H)-TGGGDGYVCVEWARCPTCK-(OH);
         (residues 32-50 of SEQ ID NO:8)

(Ac)-EGYV(Dpr)VEWARCPTCR-(NH₂);
         (residues 36-50 of SEQ ID NO:9)

(Ac)-EGYVCVEWAACPTCR-(NH₂);
         (residues 36-50 of SEQ ID NO:10)

(Ac)-EGYVCVEWARCPTCK-(NH₂);
         (residues 36-50 of SEQ ID NO:11)

(Ac)-EGYVCVEWARCPTCK-(OH);
         (residues 36-50 of SEQ ID NO:11)

(Ac)-EGYVCVEWARCPTCR-(NH₂);
         (residues 36-50 of SEQ ID NO:12)

(Ahx)-EGYVCVEWARCPTCR-(NH₂);
         (residues 36-50 of SEQ ID NO:12)

(H)-EGYVCVEFARCPTCG-(NH₂);
         (residues 36-50 of SEQ ID NO:13)

-continued
         (H)-EGYVCVEFARCPTCR-(OH);
         (residues 36-50 of SEQ ID NO:14)

(H)-EGYVCVEWARCPTCG-(NH₂);
         (residues 36-50 of SEQ ID NO:15)

(H)-EGYVCVEWARCPTCK-(NH₂);
         (residues 36-50 of SEQ ID NO:11)

(H)-EGYVCVEWARCPTCK-(OH);
         (residues 36-50 of SEQ ID NO:11)

(Ac)-EGYVCVEWARCPTCR-(OH);
         (residues 36-50 of SEQ ID NO:12)

(H)-EGYVCVEWARCPTCR-(NH₂);
         (residues 36-50 of SEQ ID NO:12)

-continued
         (H)-EGYVCVEWARCPTCR-(OH);
         (residues 36-50 of SEQ ID NO:12)

(H)-EGYVKVEWARCPTCR-(OH);
         (residues 36-50 of SEQ ID NO:16)

(H)-GYVCVEFARCPTCG-(NH₂);
         (residues 37-50 of SEQ ID NO:17)

and (H)-GYVCVEWARCPTCR-(OH);
         (residues 37-50 of SEQ ID NO:18)
``` where —(NH₂) indicates that the carboxy terminus of the compound has been amidated; where —(OH) indicates that the carboxy terminus of the compound has not been derivatized; where (Ac)-indicates that the amino terminus of the compound has been acetylated; and where (Ahx)-indicates that the amino terminus of the compound has been acylated with aminohexanoic acid.

Another embodiment is directed towards those compounds having an intramolecular disulfide linkage between two Cys residues.

More preferably, this invention provides dimers of the above sequences. These dimers can be formed via intermolecular disulfide, amide, carbamate, or urea linkages. The dimeric compounds may also contain intramolecular cysteine linkages, as well.

Most preferably, the monomeric subunits will be dimerized to yield compounds having both intramolecular and intermolecular disulfide bonds as follows:

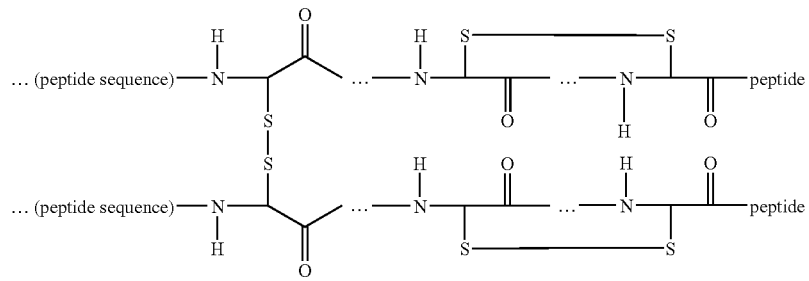

Preferably, the compound is covalently attached to one or more of a variety of hydrophilic polymers. The hydrophilic polymer(s) may be attached, for example, to one or both of the peptide chains in the dimeric compounds. If a hydrophilic polymer is attached to both peptide chains, the polymers may be the same or different, preferably they will be the same. Preferably, such attachment is at the amino terminus of the compound. It will be appreciated by those of skill in the art that when the compounds are attached to one or more of a variety of hydrophilic polymers at the amino terminus (i.e., at X₁), then X₁ is the hydrophilic polymer residue. The hydrophilic polymer has an average molecular weight of between about 500 to about 40,000 daltons, and more preferably, between about 5,000 and 20,000 daltons.

Preferably, the hydrophilic polymer is selected from the group consisting of polyethylene glycol (PEG), polypropylene glycol, polylactic acid, polyglycolic acid and copolymers thereof. Most preferably, the polymer is polyethylene glycol. A compound to which PEG is conjugated is herein termed "PEGylated."

In a preferred embodiment, a peptide is conjugated to a PEG polymer, preferably at the amino terminus. The peptide may be a dimer comprising PEGylated peptides.

The invention also provides for pharmaceutical compositions comprising one or more of the compounds described herein and a physiologically acceptable carrier. These pharmaceutical compositions can be in a variety of forms including oral dosage forms, as well as inhalable powders and solutions and injectable and infusible solutions.

Suitable pharmaceutically acceptable derivatives of the compounds include pharmaceutically acceptable salts and acid addition salts, pharmaceutically acceptable esters, pharmaceutically acceptable amides, labeled compounds and compounds that are covalently attached to one or more of a variety of hydrophilic polymers as defined hereinafter.

The peptides and peptide mimetics of the invention are useful for therapeutic purposes in treating conditions mediated by IL-5 or involving improper production of or response to IL-5 and can be used to inhibit production and accumulation of eosinophils.

These compounds will find particular use in the treatment of asthma. Thus, the present invention also provides a method for treating a patient having a disorder that is susceptible to treatment with a IL-5 inhibitor, wherein the patient receives, or is administered, a therapeutically effective dose or amount of a compound of the present invention.

A further aspect of the invention is drawn to a methods for treating conditions mediated by IL-5 or involving improper production of or response to IL-5 or for inhibiting production and accumulation of eosinophils comprising the steps of administering a compound that effects homodimerization of the alpha chain of the IL-5 receptor, thus preventing alpha chain participation in the IL-5/alpha chain/beta chain complex required for IL-5 signal transduction. Preferably, these compounds are dimeric in structure wherein each monomeric subunit is capable of binding to the alpha chain of the IL-5 receptor.

Peptides and peptide mimetics suitable for therapeutic and/or diagnostic purposes have an IC,o of about 2 mM or less, as determined by the binding affinity assay set forth below wherein a lower IC50 correlates to a stronger binding affinity to IL-5R. For pharmaceutical purposes, the peptides and peptidomimetics preferably have an IC50 of no more than about 100 uM.

When used for diagnostic purposes, the peptides and peptide mimetics preferably are labeled with a detectable label and, accordingly, the peptides and peptide mimetics without such a label serve as intermediates in the preparation of labeled peptides and peptide mimetics.

Peptides meeting the defined criteria for molecular weight and binding affinity for IL-5R comprise 15 or more amino acids wherein the amino acids are naturally occurring or synthetic (non-naturally occurring) amino acids. Peptide mimetics include peptides having one or more of the following modifications:

peptides wherein one or more of the peptidyl [—C(O)NR—] linkages (bonds) have been replaced by a non-peptidyl linkage such as a —CH2-carbamate linkage [—CH2—OC(O)NR—]; a phosphonate linkage; a —CH2-sulfonamide [—CH2—S(O)2NR—] linkage; a urea [—NHC(O)NH—] linkage; a —CH2-secondary amine linkage; or an alkylated peptidyl linkage [—C(O)NR6— where R6 is lower alkyl];

peptides wherein the N-terminus is derivatized to a —NRR, group; to a —NRC(O)R group; to a —NRC(O)OR group; to a —NRS group; to a —NHC(O)NHR group where R and R, are hydrogen or lower alkyl with the proviso that R and R, are not both hydrogen; to a succinimide group; to a benzyloxycarbonyl-NH-(CBZ-NH—) group; or to a benzyloxycarbonyl-NH-group having from 1 to 3 substituents on the phenyl ring selected from the group consisting of lower alkyl, lower alkoxy, chloro, and bromo; or peptides wherein the C terminus is derivatized to —C(O)R2 where R2 is selected from the group consisting of lower alkoxy, and —NR3R4 where R3 and R4 are independently selected from the group consisting of hydrogen and lower alkyl.

Accordingly, preferred peptides and peptide mimetics comprise a compound having a binding affinity to IL-5R as expressed by an Iqo of no more than about 100 uM, wherein from zero to all of the —C(O)NH— linkages of the peptide have been replaced by a linkage selected from the group consisting of a —CH2OC(O)NR— linkage; a phosphonate linkage; a —CH2S(O)2NR-linkage; a -CHNR-linkage; and a —C(O)NR6— linkage; and a —NHC(O)NH— linkage where R is hydrogen or lower alkyl and R6 is lower alkyl, further wherein the N-terminus of said peptide or peptide mimetic is selected from the group consisting of a —NRR, group; a —NRC(O)R group; a —NRC(O)OR group; a —NRS(O)2R group; a —NHC(O) NHR group; a succinimide group; a benzyloxycarbonyl-NHgroup; and a benzyloxycarbonyl-NH-group having from 1 to 3 substituents on the phenyl ring selected from the group consisting of lower alkyl, lower alkoxy, chloro, and bromo, where R and R, are independently selected from the group consisting of hydrogen and lower alkyl, and still further wherein the C-terminus of said peptide or peptide mimetic has the formula —C(O)R2 where R2 is selected from the group consisting of hydroxy, lower alkoxy, and —NR3R4 where R3 and R4 are independently selected from the group consisting of hydrogen and lower alkyl and where the nitrogen atom of the —NR3R4 group can optionally be the amine group of the N-terminus of the peptide so as to form a cyclic peptide, and physiologically acceptable salts thereof.

In a related embodiment, the invention is directed to a labeled peptide or peptide mimetic comprising a peptide or peptide mimetic described as above having covalently attached thereto a label capable of detection.

MODES FOR CARRYING OUT THE INVENTION DEFINITIONS AND NOMENCLATURE

Figure 1:
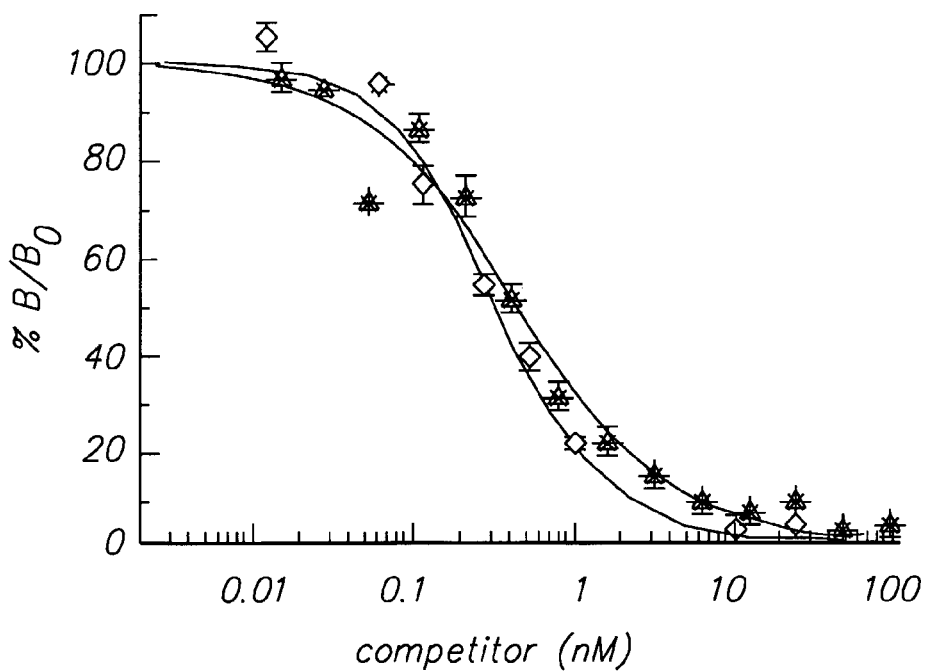
FIG. 1 shows the results of a competitive binding experiment demonstrating blockade of IL-5 binding by AF 18748.

The following definitions are set forth to illustrate and define the meaning and scope of the various terms used to describe the invention herein.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., ed., (1985) Design of Prodrug, Elsevier Science Publishers, Amsterdam.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., supra. These esters are typically formed from the corresponding carboxylic acid and an alcohol. Generally, ester formation can be accomplished via conventional synthetic techniques. (See, e. g., March, Advanced Organic Chemistry, 3rd Ed., John Wiley & Sons, New York (1985) p. 1157 and references cited therein, and Mark et al., Encyclopedia of Chemical Technology. John Wiley & Sons, New York (1980).) The alcohol component of the ester will generally comprise (i) a C2-C, 2 aliphatic alcohol that can or can not contain one or more double bonds and can or can not contain branched carbon chains or (ii) a C7-C, 2 aromatic or heteroaromatic alcohols.

This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., supra. These amides are typically formed from the corresponding carboxylic acid and an amine.

Generally, amide formation can be accomplished via conventional synthetic techniques.

(See, e. g., March, Advanced Organic Chemistry, 3rd Ed., John Wiley & Sons, New York (1985) p.1152 and Mark et al., Encyclopedia of Chemical Technology. John Wiley & Sons, New York (1980).) This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently.

That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Therapeutically or pharmaceutically effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. In addition, the abbreviation Nal is used to denote 1-naphthylalanine In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J., Adv. Drug Res. 15: 29 (1986); Veber and Freidinger, TINS p. 392 (1985); and Evans et al., J. Med. Chem. 30: 1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i. e., a polypeptide that has a biological or pharmacological activity), such as naturally-occurring receptor-binding polypeptide, but have one or more peptide linkages optionally replaced by a linkage selected from the group consisting of: —CH2NH—, —CH2S—, —CH2—CH2—,—CH═CH— (cis and trans), —COCH2—, —CH(OH)CH2—, and —CH2SO—, by methods known in the art and further described in the following references: Spatola, A. F. in Chemistry and Biochemistry of Amino Acids, Peptides and Proteins, B. Weinstein, eds., Marcel Dekker, New York, p. 267 (1983); Spatola, A. F., Vega Data (March 1983), Vol. 1, Issue 3, PEPTIDE BACKBONE MODIFICATIONS (general review); Morley, Trends Pharm Sci (1980) pp. 463-468 (general review); Hudson, D. et al., Int J Pept Prot Res 14: 177-185 (1979): (—CH2NH—, CH2CH2—); Spatola et al., Life Sci 38: 1243-1249 (1986): (—CH2—S); Hann J. Chem. Soc. Perkin Trans. I307-314 (1982): (—CH—CH—, cis and trans); Almquist et al., J Med Chem 23: 1392-1398 (1980): (—COCH2—); Jennings-White et al., Tetrahedron Lett 23: 2533 (1982): (—COCH2—); Szelke et al., European Application. EP 45665 CA: 97: 39405 (1982) (—CH(OH)CH2—); Holladay et al., Tetrahedron Lett 24: 4401-4404 (1983): (—C(OH)CH2—); and Hruby Life Sci 31: 189-199 (1982): (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e. g., a broad-spectrum of biological activities), reduced antigenicity, and others. Labeling of peptidomimetics usually involves covalent attachment of one or more labels, directly or through a spacer (e. g., an amide group), to non-interfering position(s) on the peptidomimetic that are predicted by quantitative structure-activity data and/or molecular modeling. Such non-interfering positions generally are positions that do not form direct contacts with the macromolecules (s) (e. g., immunoglobulin superfamily molecules) to which the peptidomimetic binds to produce the therapeutic effect. Derivatization (e. g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i. e., are agonistic or antagonistic to one or more receptor-mediated phenotypic changes).

Systematic substitution of one or more amino acids of a consensus sequence with a D-amino acid of the same type (e. g., D-lysine in place of L-lysine) may be used to generate more stable peptides.

For the avoidance of doubt, the abbreviation

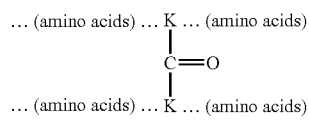

whenever used herein is meant to indicate the structure wherein the side chain amino residues of each lysine are coupled via a urea linkage.

Overview

The present invention provides compounds that bind to the IL-5R. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor. The present invention also provides compositions comprising an effective IL-5R binding, IL-5 blocking compound, and more particularly a compound, that is useful for treating disorders associated with the overexpression of IL-5 or with the production and accumulation of eosinophils.

Identification of Peptides which Bind IL-5R

A. The Receptor

The immobilized a chain, p chain, and heterodimer, as well as the extracellular domains of the single chains of the IL-5 receptors were produced in recombinant host cells. The DNA encoding IL-5R was obtained by PCR of cDNA from TF-1 cells using primers obtained from the published receptor sequences. See Murata (1992) J. Exp. Med. 175: 341-351 and Hayashida (1990) Proc. Natl. Acad. Sci. USA 87: 9655-9659, each of which is incorporated herein by reference. One useful form of IL-5R is constructed by expressing the protein as a soluble protein in baculovirus transformed host cells using standard methods; another useful form is constructed with a signal peptide for protein secretion and for glycophospholipid membrane anchor attachment. This form of anchor attachment is called "PIG-tailing." See Caras and Wendell, Science 243: 1196-1198 (1989) and Lin et al., Science 249: 677-679 (1990).

Using the PIG-tailing system, one can cleave the receptor from the surface of the cells expressing the receptor (e. g., transformed CHO cells selected for high level expression of receptor with a cell sorter) with phospholipase C. The cleaved receptor still comprises a carboxy terminal sequence of amino acids, called the "HPAP tail," from the signal protein for membrane attachment and can be immobilized without further purification. The recombinant receptor protein can be immobilized by coating the wells of microtiter plates with an anti-HPAP tail antibody (Ab 179), blocking non-specific binding with bovine serum albumin (BSA) in PBS, and then binding cleaved recombinant receptor to the antibody. Using this procedure, one should perform the immobilization reaction in varying concentrations of receptor to determine the optimum amount for a given preparation, because different preparations of recombinant protein often contain different amounts of the desired protein. See U.S. patent application Ser. No. 07/947,339, filed Sep. 18, 1992, incorporated herein by reference.

To discriminate among higher affinity peptides, a monovalent receptor probe frequently is used. This probe can be produced using protein kinase A to phosphorylate a peptide sequence fused to the C-terminus of the soluble receptor. The "engineered" form of the IL-5 receptor a chain and β chain are then expressed in host cells, typically CHO cells.

Following PI-PLC harvest of the receptors, the receptor is labeled to high specific activity with 33P or 32p for use as a monovalent probe to identify high affinity ligands using colony lifts.

cl. The Peptides

Preferred methods to facilitate identification of peptides which bind IL-5R involve first identifying lead peptides which bind the receptor and then making other peptides which resemble the lead peptides.

A representative listing of preferred compounds of the invention is shown in Tables 1 and 2 below.

TABLE 1

| | |
|---|---|
| $X_1$-TGGGDGYV$X_3$VE$X_4$ARCPTCK-$X_2$; | (residues 32-50 of SEQ ID NO:1) |
| $X_1$-EGYV$X_3$VE$X_4$ARCPTCK-$X_2$; | (residues 36-50 of SEQ ID NO:2) |
| $X_1$-EGYV$X_3$VE$X_4$ARCPTCR-$X_2$; | (residues 36-50 of SEQ ID NO:3) |
| $X_1$-GYV $X_3$VE$X_4$ARCPTCG-$X_2$; | (residues 36-50 of SEQ ID NO:4) |
| $X_1$-EGYV$X_3$VE$X_4$ARCPTCG-$X_2$; | (residues 36-50 of SEQ ID NO:5) |
| $X_1$-GYV$X_3$VE$X_4$ARCPTCR-$X_2$; | (residues 37-50 of SEQ ID NO:6) |
| and | |
| $X_1$-EGYV$X_3$VE$X_4$AACPTCR-$X_2$ | (residues 36-50 of SEQ ID NO:7) | wherein $X_1$ is hydrogen or acyl; $X_2$ is-NH$_2$ or-OH wherein-NH2 indicates that the carboxy terminus of the compound has been amidated and —OH indicates that the carboxy terminus of the compounds has not been derivitized; $X_3$ is Cys, Lys, or Dpr wherein Dpr is diaminopropionic acid, and $X_4$ is Nal, Trp, or Phe. Another embodiment is directed towards those compounds an intramolecular disulfide linkage between two cysteine residues.

Particularly preferred compounds include the following:

TABLE 2

| | |
|---|---|
| (H)-TGGGDGYVCVEWARCPTCK-(OH); | (residues 32-50 of SEQ ID NO:8) |
| (Ac)-EGYV(Dpr)VEWARCPTCR-(NH$_2$); | (residues 36-50 of SEQ ID NO:9) |
| (Ac)-EGYVCVEWAACPTCR-(NH$_2$); | (residues 36-50 of SEQ ID NO:10) |

TABLE 2-continued

| | |
|---|---|
| (Ac)-EGYVCVEWARCPTCK-(NH$_2$); | (residues 36-50 of SEQ ID NO:11) |
| (Ac)-EGYVCVEWARCPTCK-(OH); | (residues 36-50 of SEQ ID NO:11) |
| (Ac)-EGYVCVEWARCPTCR-(NH$_2$); | (residues 36-50 of SEQ ID NO:12) |
| (Ahx)-EGYVCVEWARCPTCR-(NH$_2$); | (residues 36-50 of SEQ ID NO:12) |
| (H)-EGYVCVEFARCPTCG-(NH$_2$); | (residues 36-50 of SEQ ID NO:13) |
| (H)-EGYVCVEFARCPTCR-(OH); | (residues 36-50 of SEQ ID NO:14) |
| (H)-EGYVCVEWARCPTCG-(NH$_2$); | (residues 36-50 of SEQ ID NO:15) |
| (H)-EGYVCVEWARCPTCK-(NH$_2$); | (residues 36-50 of SEQ ID NO:11) |
| (H)-EGYVCVEWARCPTCK-(OH); | (residues 36-50 of SEQ ID NO:11) |
| (Ac)-EGYVCVEWARCPTCR-(OH); | (residues 36-50 of SEQ ID NO:12) |
| (H)-EGYVCVEWARCPTCR-(NH$_2$); | (residues 36-50 of SEQ ID NO:12) |
| (H)-EGYVCVEWARCPTCR-(OH); | (residues 36-50 of SEQ ID NO:12) |
| (H)-EGYVKVEWARCPTCR-(OH); | (residues 36-50 of SEQ ID NO:16) |
| (H)-GYVCVEFARCPTCG-(NH$_2$); | (residues 37-50 of SEQ ID NO:17) |
| and | |
| (H)-GYVCVEWARCPTCR-(OH); | (residues 37-50 of SEQ ID NO:18) | where —(NH$_2$) indicates that the carboxy terminus of the compound has been amidated; Where —(OH) indicates that the carboxy terminus of the compound has not been derivatized; where (Ac)— indicates that the amino terminus of the compound has been acetylated; and where (Ahx)-indicates that the amino terminus of the compound has been acylated with aminohexanoic acid.

More preferably, this invention provides dimers of the above sequences. For example, a sidechain primary amino group of one monomeric subunit can be coupled to a sidechain primary amino group of a second monomeric subunit via a urea linkage.

Likewise, one of skill in the art will readily appreciate that side chain functionality of one monomeric subunit can be coupled to side chain functionality of a second subunit through a variety of strategies, including without limitation, intermolecular disulfide, ester, amide, carbamate, or urea linkages.

Particularly preferred compounds include disulfide linked dimers of the above compounds which also have one or more intramolecular disulfide bonds. Most preferred are dimers having the following pattern of disulfide linkages:

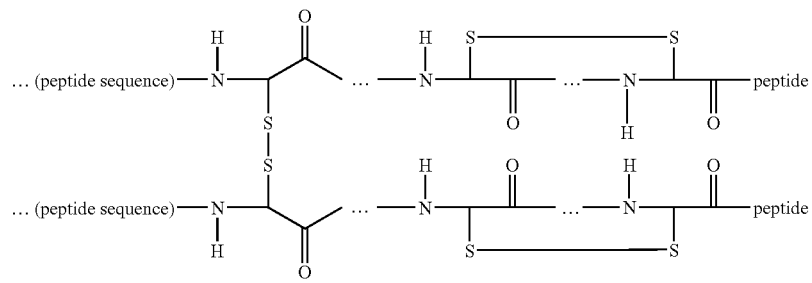

C. Affinity

A variety of methods can be used to evaluate $IC_{50}$ values. For example, binding assays were used to determine whether the peptides inhibit the binding of IL-5 to the extracellular domain of the IL-5 receptor a-chain. Alternatively, for some peptides, a microphysiometer assay was used to determine whether the peptide blocked the response of TF-1 cells to IL-5 (5 ng/ml).

To determine whether these peptides had any effect on IL-5 mediated signal transduction, they were tested for IL-5R agonist and antagonist activity in a microphysiometer assay using the IL-5 responsive human leukemia cell line, TF-1.

Following overnight IL-5 starvation, these cells exhibit a rapid and robust increase in metabolic activity upon addition of IL-5 to the cell culture medium. A preferred compound was tested in the TF-1 cell microphysiometer assay and found to almost completely block the response of the cells to 400 pM IL-5 when tested at 10 uM concentration. The peptide was of sufficiently high affinity to allow us to determine an accurate microphysiometer assay IC50 value.

Typically, the IC50 values were determined using the free peptide, although in some instances, it may be preferable to amidate the C-terminus or to prepare an ester or other carboxy amide. The N-terminal and C-terminal amino acids of the synthetic peptides are often preceded by one or two glycine residues. These glycines are not believed to be necessary for binding or activity.

Peptides and peptidomimetics having an IC50 of greater than about 100 mM lack sufficient binding to permit use in either the diagnostic or therapeutic aspects of this invention. Preferably, for diagnostic purposes, the peptides and peptidomimetics have an IC50 of about 2.5 mM or less and, for pharmaceutical purposes, the peptides and peptidomimetics have an IC50 of about 2 mM or less.

IV. Preparation of Peptides and Peptide Mimetics

The peptides of the invention can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e. g., Merrifield (1963) J. Am. Chem. Soc. 85: 2149. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO-BEADS SX-1 by Bio Rad Laboratories, Richmond, Calif., and the preparation of the hydroxymethyl resin is described by Bodonszky et al., Chem. Ind. (London) 38: 1597 (1966). The benzhydrylamine (BHA) resin has been described by Pietta and Marshall, Chem. Commn. 650 (1970), and is commercially available from Beckman Instruments, Inc., Palo Alto, Calif., in the hydrochloride form.

Thus, the compounds of the invention can be prepared by coupling an alpha-amino protected amino acid to the chloromethylated resin with the aid of, for example, cesium bicarbonate catalyst, according to the method described by Gisin (1973) Helv. Chim. Acta 56: 1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e. g. formyl, trifluoroacetyl, acetyl), aromatic urethane type protecting groups (e. g. benzyloxycarboyl (Cbz) and substituted Cbz), aliphatic urethane protecting groups (e. g. t-butyloxycarbonyl (Boc), isopropyloxycarbonyl, cyclohexyloxycarbonyl) and alkyl type protecting groups (e. g. benzyl, triphenylmethyl, and fluorenylmethyl oxycarbonyl (Fmoc)). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl.

The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc 2.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride (CH2Cl2), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described in Stewart, Solid Phase Peptide Syntheses (Freeman and Co., San Francisco, 1969).

In addition, in some preferred embodiments of the invention having one or more cysteine residues in the compound, one or more of the cysteines may bear an appropriate protecting group, preferably an Acm group, to prevent or hinder undesired disulfide formation.

These solid phase peptide synthesis procedures are well known in the art and further described in Stewart, Solid Phase Peptide Syntheses (Freeman and Co., San Francisco, 1969). These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxyphenylalanine, a amino acids such as L-a-hydroxylysine and D-a-methylalanine, L-a methylalanine, amino acids, and isoquinoline. D amino acids and non-naturally occurring synthetic amino acids can also be incorporated into the peptides of the present invention.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di (lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4,6, or 7 members can be employed. Cyclic groups can be saturated or unsaturated, and if unsaturated, can be aromatic or non-aromatic.

The peptides typically are synthesized as the free acid but, as noted above, could be readily prepared as the amide (i. e., designated with a —(NH2) at the carboxy terminus of the compound) or ester. One can also modify the amino and/or carboxy terminus of the peptide compounds of the invention to produce other compounds of the invention. Amino terminus modifications include methylating (i. e., —NHCH$_3$ or —NH(CH$_3$)$_2$), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. Specifically, the N-terminal amino group can then be reacted as follows:

(a) to form an amide group of the formula RC(O)NH— where R is as defined above by reaction with an acid halide [e. g., RC(O)Cl] or acid anhydride. Typically, the reaction can be conducted by contacting about equimolar or excess amounts (e. g., about 5 equivalents) of an acid halide to the peptide in an inert diluent (e. g., dichloromethane) preferably containing an excess (e. g., about 10 equivalents) of a tertiary amine, such as diisopropylethylamine, to scavenge the acid generated during reaction. Reaction conditions are otherwise conventional (e. g., room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (e. g., about 5 equivalents) can be employed and the amino group is converted to the succinimide by methods well known in the art including the use of an excess (e. g., ten equivalents) of a tertiary amine such as diisopropylethylamine in a suitable inert solvent (e. g., dichloromethane). See, for example, Wollenberg et al., U.S. Pat. No. 4,612,132 which is incorporated herein by reference in its entirety. It is understood that the succinic group can be substituted with, for example, $C_2$-$C_6$ alkyl or —SR substituents which are prepared in a conventional manner to provide for substituted succinimide at the N-terminus of the peptide. Such alkyl substituents are prepared by reaction of a lower olefin ($C_2$-$C_6$) with maleic anhydride in the manner described by Wollenberg et al., and-SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ-Cl (i. e., benzyloxycarbonyl chloride) or a substituted CBZ-Cl in a suitable inert diluent (e. g., dichloromethane) preferably containing a tertiary amine to scavenge the acid generated during the reaction;

d) to form a sulfonamide group by reaction with an equivalent amount or an excess (e. g., 5 equivalents) of R—S(O)$_2$Cl in a suitable inert diluent (dichloromethane) to convert the terminal amine into a sulfonamide where R is as defined above. Preferably, the inert diluent contains excess tertiary amine (e. g., ten equivalents) such as diisopropylethylamine, to scavenge the acid generated during reaction. Reaction conditions are otherwise conventional (e. g., room temperature for 30 minutes);

(e) to form a carbamate group by reaction with an equivalent amount or an excess (e. g., 5 equivalents) of R—OC(O)Cl or R—OC(O)OC$_6$H$_4$-p-NO$_2$ in a suitable inert diluent (e. g., dichloromethane) to convert the terminal amine into a carbamate where R is as defined above. Preferably, the inert diluent contains an excess (e. g., about 10 equivalents) of a tertiary amine, such as diisopropylethylamine, to scavenge any acid generated during reaction. Reaction conditions are otherwise conventional (e. g., room temperature for 30 minutes); and (f) to form a urea group by reaction with an equivalent amount or an excess (e. g., 5 equivalents) of R—N=C=O in a suitable inert diluent (e. g., dichloromethane) to convert the terminal amine into a urea (i. e., RNHC(O)NH—) group where R is as defined above. Preferably, the inert diluent contains an excess (e. g., about 10 equivalents) of a tertiary amine, such as diisopropylethylamine. Reaction conditions are otherwise conventional (e. g., room temperature for about 30 minutes).

In preparing peptide mimetics wherein the C-terminal carboxyl group is replaced by an ester (i. e., —C(O)OR where R is as defined above), the resins used to prepare the peptide acids are employed, and the side chain protected peptide is cleaved with base and the appropriate alcohol, e. g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR$_3$R$_4$, a benzhydrylamine resin is used as the solid support for peptide synthesis. Upon completion of the synthesis, hydrogen fluoride treatment to release the peptide from the support results directly in the free peptide amide (i. e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i. e., the C-terminus is —C(O) NRR1 where R and R1 are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the termini of the peptide, so that there is no terminal amino or carboxyl-group, to decrease susceptibility to proteases or to restrict the conformation of the peptide. C-terminal functional groups of the compounds of the present invention include amide, amide lower alkyl, amide di (lower alkyl), lower alkoxy, hydroxy, and carboxy, and the lower ester derivatives thereof, and the pharmaceutically acceptable salts thereof.

One can also readily modify peptides by phosphorylation, and other methods for making peptide derivatives of the compounds of the present invention are described in Hruby et al., Biochem J. 268 (2: 249-262 (1990), incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor (1989) Ann. Rep. Med. Chem. 24: 243-252, incorporated herein by reference. These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —CH2-carbamate linkage, a phosphonate linkage, a —CH$_2$-sulfonamide linkage, a urea linkage, a secondary amine (—CH2NH—) linkage, and an alkylated peptidyl linkage [—C(O)NR$_6$— where R$_6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O) NR— linkage in the peptide with a —CH,-carbamate linkage (—CH$_2$OC(O)NR—), then the carboxyl (—COOH) group of a suitably protected amino acid is first reduced to the —CH$_2$OH group which is then converted by conventional methods to a —OC(O)Cl functionality or a para-nitrocarbonate —OC(O)O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$-carbamate linkages, see Cho et al., Science 261: 1303-1305 (1993).

Similarly, replacement of an amido linkage in the peptide with a phosphonate linkage can be achieved in the manner set forth in U.S. Pat. Nos. 5,359,115 and 5,420,328 to Campbell et al. and in U.S. patent application Ser. No. 08/081,577, the disclosures of which are incorporated herein by reference in their entirety.

Replacement of an amido linkage in the peptide with a —CH2-sulfonamide linkage can be achieved by reducing the carboxyl (—COOH) group of a suitably protected amino acid to the —CH2OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(O)$_2$Cl functional group which replaces the carboxyl group of the otherwise suitably protected amino acid. Use of this suitably protected amino acid analogue in peptide synthesis provides for inclusion of an —CH$_2$S(O)$_2$NR-linkage which replaces the amido linkage in the peptide thereby providing a peptide mimetic. For a more complete description on the conversion of the carboxyl group of the amino acid to a —CH$_2$S(O)$_2$Cl group, see, for example, Chemistry & Biochemistry of Amino Acids, Peptides and Proteins, Boris Weinstein (ed.), Vol. 7, pp. 267-357, Marcel Dekker, Inc., New York (1983) which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —CH, NH-linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogues by reduction of the carbonyl group of the amido linkage in the dipeptide is well known in the art.

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di (lower alkyl), lower alkoxy, hydroxy, and carboxy, and the lower ester derivatives thereof, and the pharmaceutically acceptable salts thereof.

V. Derivatives Having Disulfide Bonds

The compounds of the present invention may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine. These intramolecular or intermolecular disulfide derivatives can be represented schematically as shown below:

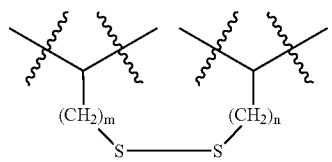

wherein m and n are independently 1 or 2.

Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the art as shown below:

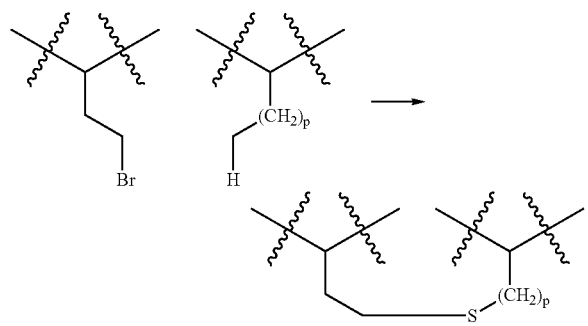

wherein p is 1 or 2. One of skill in the art will readily appreciate that this displacement can also occur using other homologs of the a-amino-y-butyric acid derivative shown above and homocysteine.

Alternatively, the amino-terminus of the peptide can be capped with an alpha-substituted acetic acid, wherein the alpha substituent is a leaving group, such as an a-haloacetic acid, for example, a-chloroacetic acid, a-bromoacetic acid, or a-iodoacetic acid. The compounds of the present invention can be cyclized or dimerized via displacement of the leaving group by the sulfur of the cysteine or homocysteine residue. See, e. g., Barker et al., J. Med Chem. 35: 2040-2048 (1992) and Or et al., J. Org. Chem. 56: 3146-3149 (1991), each of which is incorporated herein by reference.

VI. Hydrophilic Polymer Addition

In addition to the foregoing N-terminal and C-terminal modifications, the compounds of the invention, including peptidomimetics, can advantageously be modified with or covalently coupled to one or more of a variety of hydrophilic polymers. The corresponding derivative may have increased solubility and circulation half-lives and masked immunogenicity. Nonproteinaceous polymers suitable for use in accordance with the present invention include, but are not limited to, polyalkylethers as exemplified by polyethylene glycol and polypropylene glycol; polylactic acid; polyglycolic acid; polyoxyalkenes; polyvinylalcohol; polyvinylpyrrolidone; cellulose and cellulose derivatives; dextran and dextran derivatives; etc. Generally, such hydrophilic polymers have an average molecular weight ranging from about 500 to about 100,000 daltons, more preferably from about 2000 to about 40,000 daltons, and even more preferably, from about 5,000 to about 20,000 daltons. In preferred embodiments, such hydrophilic polymers have an average molecular weight of about 5,000 daltons, 10,000 daltons, or 20,000 daltons.

The compounds of the invention can be derivatized with or coupled to such polymers using any of the methods set forth in Zallipsky Bioconjugate Chem. 6: 150-165 (1995); Monfardini et al., Bioconjugate Chem. 6: 62-69 (1995); U.S. Pat. Nos. 4,640,835; 4,496,689; 4,301,144; 4,670,417; 4,791,192; 4,179,337 or WO 95/34326.

In a presently preferred embodiment, the compounds of the present invention are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the compounds of the present invention can be either branched or unbranched. See, e. g., Monfardini et al., Bioconjugate Chem. 6: 62-69 (1995). PEGs are commercially available from Shearwater Polymers Inc. (Huntsville, Ala.), Sigma Chemical Co., and other companies. Such PEGs include, but are not limited to, monomethyoxypolyethylene glycol (MePEG-OH); monomethoxypolyethylene glycol-succinate (MePEG-S); monomethoxypolyethylene glycol-succinimidyl succinate (MePEG-S-NHS); monomethoxypolyethylene glycol amine (MePEG-NH$_2$); monomethoxypolyethylene glycol-tresylate (MePEG-TRES); and monomethoxypolyethylene glycol-imidazolyl-carbonyl (MePEG-IM).

Briefly, in one exemplar embodiment, the hydrophilic polymer which is employed, e. g., PEG, is preferably capped at one end by an unreactive protecting group, such as a methoxy or ethoxy. Thereafter, the polymer is activated at the other end by reaction with a suitable activating agent, such as cyanuric halide (e. g., cyanuric chloride, bromide, or fluoride), diimadozole, an anhydride reagent (e. g., a dihalosuccinic anhydride, such as dibromosuccinic anhydride), acyl azide, p-diazoiumbenzyl ether), 3-(p-diazoniumphenoxy)-2-hydroxypropylether and the like. The activated polymer is then reacted with a compound of the present invention to produce a compound derivatized with a polymer. The amount of derivatization will be dependent, in part, upon the availability of free amine groups in the compound of the present invention. For example, if all but one of the primary amine groups of the compound is protected, e. g., by an acyl group, a monoPEGylated compound will be formed. In a preferred embodiment of the invention, the amino terminus of a peptide or peptide mimetic compound is derivatized with PEG.

Alternatively, a functional group in the compounds of the invention can be activated for reaction with the polymer, or the two groups can be joined in a concerted coupling reaction using known coupling methods. It will be readily appreciated that the compounds of the invention can be derivatized with PEG using a myriad of other reaction schemes known to and used by those of skill in the art.

VII. Dimerization

One embodiment of this invention is drawn to dimers wherein side chain amino groups of each monomeric subunit are coupled via a urea linkage. Other embodiments are drawn to dimers wherein side chain amino groups of each monomeric subunit are coupled via disulfide, amide, or carbamate linkages. The dimeric compounds may also contain intramolecular cysteine linkages. Most preferably, the monomeric subunits will be dimerized to yield compounds having both intramolecular and intermolecular disulfide bonds. These dimers can be prepared as described below using techniques known to those of skill in the art and appropriate protecting group strategies.

In a preferred embodiment of the invention, a dimeric compound is derivatized with a hydrophilic polymer, such as PEG. One or both of the monomers may be derivatized with a hydrophilic polymer. In a more preferred embodiment, the compound comprises a dimer with PEG covalently bound to the amino termini of both of the monomers.

VIII. In Vivo and In Vitro Testing

The activity of the compounds of the present invention can be evaluated in vivo in one of the numerous animal models of asthma. See Larson, "Experimental Models of Reversible Airway Obstruction," in The Lung: Scientific Foundations, Crystal, West et al., eds., Raven Press, New York, 1991; Warner et al., Am. Rev. Respir. Dis. 141: 253-257 (1990). An ideal animal model would duplicate the chief clinical and physiological features of human asthma, including: airway hyperresponsiveness to chemical mediators and physical stimuli; reversal of airway obstruction by drugs useful in human asthma (p-adrenergics, methylxanthines, corticosteroids, and the like); airway inflammation with infiltration of activated leukocytes; and chronic inflammatory degenerative changes, such as basement membrane thickening, smooth muscle hypertrophy, and epithelial damage.

Species used historically as animal models include mice, rats, guinea pigs, rabbits, dogs, and sheep. All have some limitations, and the proper choice of animal model depends upon the question which is to be addressed.

The initial asthmatic response can be evaluated in guinea pigs, and dogs, and particularly, with a basenji-greyhound cross strain which develops nonspecific airway hyperresponsiveness to numerous nonallergenic substances, such as methacholine and citric acid. Certain selected sheep exhibit a dual response after antigen challenge with Ascaris proteins. In dual responding animals, the initial asthmatic response (IAR) is followed by a late asthmatic response (LAR) at 6-8 hours post-exposure. Hypersensitivity to the cholinergic agonist carbachol increases at 24 hours after antigen challenge in those animals which exhibit LAR.

The allergic sheep model can be used to evaluate the potential antiasthmatic effects of the compounds of the present invention. Administration of compositions comprising aerosolized solutions of the compounds of the instant invention to allergic sheep prior to or following exposure to specific allergens will demonstrate that such compositions substantially lessen or abolish the late asthmatic response and consequent hyperresponsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, rheumatoid spondylitis, osteoarthritis, gouty arthritis and other arthritic conditions, inflammatory bowel disease, peptic ulcer and various skin conditions.

The efficacy of the compounds of the instant invention for the treatment of the vast majority of immunomediated inflammatory disorders can be evaluated by either in vitro or in vivo procedures. Thus, the anti-inflammatory efficacy of the compounds of the instant invention can be demonstrated by assays well known in the art, for example, the Reversed Passive Arthus Reaction (RPAR)-PAW technique (see, e. g., Ganguly et al., U.S. Pat. No. 5,126,352, (1992)). Assays for determining the therapeutic value of compounds in the treatment of various skin conditions, such as hyperproliferative skin disease, are well known in the art, for example, the Arachidonic Acid Mouse Ear Test (Id.). The compounds of the instant invention can be evaluated for their antiulcer activity according to the procedures described in Chiu et al., Archives Internationales de Pharmacodynamie et de Therapie 270: 128-140 (1984).

IX. In Vitro Uses

The compounds of the invention are useful in vitro as unique tools for understanding the biological role of IL-5, including the evaluation of the many factors thought to influence, and be influenced by, the production of IL-5 and the receptor binding process. The present compounds are also useful in the development of other compounds that bind to the IL-5R, because the present compounds provide important information on the relationship between structure and activity that should facilitate such development.

The compounds are also useful as competitive inhibitors or tracers in assays to screen for new IL-5 receptor blockers. In such assay embodiments, the compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as ['25I], enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization.

Possibilities for indirect labeling include biotinylation of one constituent followed by binding to avidin coupled to one of the above label groups. The compounds may also include spacers or linkers in cases where the compounds are to be attached to a solid support.

Thus, the compositions and methods of the present invention also can be used in vitro for testing a patient's susceptibility to varying treatment regimens for disorders associated with the overproduction of IL-5 or an improper response to IL-5 using an in vitro diagnostic method whereby a specimen is taken from the patient and is treated with a IL-5R binding, IL-5 blocking compound of the present invention to determine the effectiveness and amount of the compound necessary to produce the desired effect. The blocking compound and dosage can be varied. After the blocking compounds are screened, then the appropriate treatment and dosage can be selected by the physician and administered to the patient based upon the results. Therefore, this invention also contemplates use of a blocking compound of this invention in a variety of diagnostic kits and assay methods.

A further aspect of the invention is the use of compounds of the present inventions for the manufacture of a medicament for the treatment and/or prevention of a variety of IL-5 disorders.

X. In Vivo Uses

The compounds of the invention can also be administered to warm blooded animals, including humans, to block the binding of IL-5 to the IL-5R in vivo. Thus, the present invention encompasses methods for therapeutic treatment of IL-5 related disorders that comprise administering a compound of the invention in amounts sufficient to block or inhibit the binding of IL-5 to the IL-5R in vivo. For example, the peptides and compounds of the invention can be administered to treat symptoms related to the overproduction of IL-5 or an improper response to IL-5. The compositions and methods described herein will find use for the treatment and/or prevention of a variety of IL-5 related disorders.

According to one embodiment, the compositions of the present invention are useful for preventing or ameliorating asthma. In using the compositions of the present invention in a treatment of asthma, the compounds typically will be administered prophylactically prior to exposure to allergen or other precipitating factor, or after such exposure. The compounds of the instant invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like.

Accordingly, the present invention also provides pharmaceutical compositions comprising, as an active ingredient, at least one of the peptides or peptide mimetics of the invention in association with a pharmaceutical carrier or diluent. The compounds of this invention can be administered by oral, pulmonary, parenteral (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration.

Typically, when the compounds of the instant invention are to be used in the treatment of asthma, they will be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insulation from an inhaler device, for example.

For solutions used in making aerosols of the present invention, the preferred range of concentration of the compounds of the instant invention is 0.1-100 milligrams (mg)/milliliter (mL), more preferably 0.1-30 mg/mL, and most preferably, 1-10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic.

Suspensions of the compounds of the present invention in hydrofluoronalkane propellants, especially 1,1,1,2-tetrafluoroethane of 1,1,1,2,3,3,3-heptafluoropropane, optionally in the presence of a surfactant and/or cosolvent (e. g., ethanol) in a pressurized canister may also be provided together with a suitable delivery device for the treatment of the above mentioned respiratory disorders, especially asthma and allergic rhinitis.

Formulation of such solutions for creating aerosol inhalants is discussed in Remington's Pharmaceutical Sciences, see also, Ganderton and Jones, Drug Delivery to the Respiratory Tract, Ellis Horwood (1987); Gonda Critical Reviews in Therapeutic Drug Carrier Systems 6: 273-313 (1990); and Raeburn et al., J. Pharmacol. Toxicol. Methods 27: 143-159 (1992).

Solutions of the compounds of the instant invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the instant invention connected to or contained within any of the conventional means for creating aerosols in asthma medication, such as metered dose inhalers, jet nebulizers, or ultrasonic nebulizers. Optionally such device may include a mouthpiece fitted around the orifice.

In an embodiment for the treatment of allergic rhinitis, a device may comprise a solution of a compound of the instant invention in a nasal sprayer.

A dry powder comprising a compound of the instant invention, optionally with an excipient, is another embodiment of the present invention. This may be administered by a drug powder inhaler containing the above described powder.

The compounds of the inventions can also be used in the treatment of immunomediated inflammatory skin conditions, such as urticaria and angioedema, eczematous dermatitis, and hyperproliferative skin disease, e. g., psoriasis, in mammals. As a result of the topical administration of a compound of the present invention, a remission of the symptoms can be expected. Thus, one affected by an immunomediated inflammatory skin condition can expect a decrease in scaling, erythema, size of the plaques, pruritus, and other symptoms associated with the skin condition. The dosage of medicament and the length of time required for successfully treating each individual patient may vary, but those skilled in the art will be able to recognize these variations and adjust the course of therapy accordingly.

Also included within the invention are preparations for topical application to the skin comprising a compound of the present invention, typically in concentrations in the range of from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e. g., talc, lactose, starch, and the like. Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e. g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e. g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

It should, of course, be understood that the compositions and methods of this invention can be used in combination with other agents exhibiting the ability to modulate IL-5 synthesis, release, and/or binding and with other agents for the treatment of immunomediated inflammatory disorders, and particularly asthma. ss-Adrenergic agonists are especially useful in these combinations, because they provide symptomatic relief of the initial asthmatic response, whereas the compounds of the present invention provide relief for the late asthmatic response. Preferred p-adrenergic agonists in these solutions include any of the usual P-agonists employed for the relief of asthma, such as albuterol, terbutaline, formoterol, fanoterol, or prenaline.

Other agents useful in combination with the compounds of the instant invention include anticholinergics, such as ipratropium bromide, and anti-inflammatory corticosteroids (adrenocortical steroids) such as beclomethasone, triamcinolone, flurisolide, or dexamethasone.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

The quantities of the IL-5 blocking compound necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e. g., in Gilman et al., (eds), Goodman and Gilman's: The Pharmacological Basis of Therapeutics, 8th ed., Pergamon Press (1990); and Remington's Pharmaceutical Sciences, 7th ed., Mack Publishing Co., Easton, Pa. (1985).

The peptides and peptide mimetics of this invention are effective in treating IL-5 mediated conditions when administered at a dosage range of from about 0.001 mg to about 10 mg/kg of body weight per day. The specific dose employed is regulated by the particular condition being treated, the route of administration as well as by the judgement of the attending clinician depending upon factors such as the severity of the condition, the age and general condition of the patient, and the like.

Many ligand-binding receptors are comprised of multiple subunits. Where the ligand binding and the signal transduction activities of the receptor are found on different subunits, receptor activation may be reduced or abolished by compounds that interfere with the association of the ligand-binding subunits with the signal-transducing subunits. It is herein disclosed that compounds that bind with high affinity to two or more ligand-binding subunits of heteromeric receptors are effective receptor antagonists. It has been discovered that providing a multivalent compound effective to bind with high affinity to two or more ligand-binding subunits of a receptor macromolecule is effective to antagonize the action of a ligand at a receptor. For example, the IL-5 receptor comprises an a subunit and a ss subunit, where the P subunit is the signal-transducing subunit. Compounds binding to two IL-5 a subunits are herein disclosed to be potent, highly specific IL-5 receptor antagonists.

Compounds that bind with high affinity to two a subunits of the interleukin 3 (IL-3) receptor and compounds that bind with high affinity to two a subunits of the granulocyte/macrophage colony-stimulating factor (GM-CSF) receptor are likewise expected to be potent, highly specific receptor antagonists. The protein gp130 is the common signaling subunit for the heteromeric receptors of a number of different ligands, such as interleukin 6 (IL-6), leukemia inhibitory factor (LIF), oncostatin M, interleukin 12 (IL-12), and ciliary neurotrophic factor (CNTF). Compounds that dimerize the ligandbinding subunits of these receptors would be very effective antagonists. The interleukin 2 (IL-2) receptor is also a heteromeric receptor with distinct ligand-binding and signaling subunits suitable for antagonism by compounds that bind with high affinity to two ligandbinding IL-2 subunits.

A method for identifying compounds that dimerize to ligand-binding receptor subunits involves the following steps listed below. Firstly, peptide libraries are screened against the ligand-binding receptor subunit, using suitable screening methods known in the art and as disclosed above. Clones that compete with ligands for binding at the target receptor are identified in this screening step. Next, those clones with an odd number of cysteine residues are identified. Peptides from the clones with an odd number of cysteine residues are then synthesized, with the cysteine (s) in reduced form. These peptides are then allowed to oxidize in aqueous solution to form peptide dimers. Finally, these dimeric peptides are tested for dimeric binding of the receptor subunit.

Alternatively, combinatorial libraries of dimeric molecules can be screened against the ligand-binding subunit. Compounds that compete with ligand for binding should be tested to determine if the compounds dimerize to receptor subunits.

A third method comprises developing reporter cell lines that express chimeric receptors consisting of the extracellular ligand-binding domain of a homomeric receptor such as GM-CSF. An example of such a chimera is provided above (IL-SaECD). Such reporter cells would contain a reporter gene such as luciferase whose transcription is upregulated when the chimeric receptor is activated by a dimerized ligand. These cells would then be used to screen libraries of dimeric molecules as in the preceding step.

Although only preferred embodiments of the invention are specifically described above, it will be appreciated that modifications and variations of the invention are possible without departing from the spirit and intended scope of the invention.

All patents, patent applications, journal articles and other references mentioned herein, both infra and supra, are incorporated by reference in their entireties.

In these examples and throughout this specification, the abbreviations employed have their generally accepted meanings, as follows:

ABI=Applied Biosystems Inc.
BHA=benzhydrylamine resin
BSA=bovine serum albumin
DMEM=Dulbecco's Minimal Essential Medium DMEM/F12=Dulbecco's Minimal Essential Medium/Hamm's F 12 Medium
ECD=Extracellular domain
ESMS=Electrospray MS ng/ml=nanogram/milliliter min=minutes pl=microliter pl/mg=microliter/milligram hr=hours
HMP=p-hydroxymethylphenoxymethyl polystyrene resin
HPLC=High Pressure Liquid Chromatography
HBTU=O-(benzotriazol-1-yl)-1,1,3,3-tetramethyluronium hexafluorophosphate HOBt=1-hydroxybenzotriazole
IL-5=Interleukin 5 IL-SRa=the alpha chain subunit of the human IL-5 Receptor
IL-SRaECD=ECD of the human IL-5 receptor a chain
MALDI/MS=Matrix Assisted Laser Desorption Ionization MS
MS=Mass Spectrometry
PAL=5-(4-aminomethyl-3,5-dimethoxyphenoxy) valeric acid
PBS=phosphate buffered saline
RP-HPLC=Reverse Phase HPLC
Tris=Tris (hydroxymethyl) aminomethane
TNF=Tumor Necrosis Factor

EXAMPLE 1

Solid Phase Peptide Synthesis

Various peptides of the invention were synthesized using the Merrifield solid phase synthesis techniques (see Steward and Young, Solid Phase Peptide Synthesis, 2d. edition (Pierce Chemical, Rockford, Ill. (1984) and Merrifield (1963) J. Am. Chem. Soc. 85: 2149) on an Applied Biosystems Inc. Model 431A or 433A peptide synthesizer. Alternatively, a Milligen/Biosearch 9600 automated instrument could be used.

The peptides were assembled using standard protocols of the Applied Biosystems Inc. (ABI) System Software version 1.01. Each coupling was performed for one-two hours with HBTU and HOBt. Double-couplings were performed at each step.

The resin used was HMP resin or PAL resin (Milligen/Biosearch), which is a cross-linked polystyrene resin with 5-(4'-Fmoc-aminomethyl-3,5'-dimethyoxyphenoxy) valeric acid as a linker. Use of PAL resin results in a carboxyl terminal amide functionality upon cleavage of the peptide from the resin. Upon cleavage, the HMP resin produces a carboxylic acid moiety at the C-terminus of the final product. Most reagents, resins, and protected amino acids (free or on the resin) were purchased from Millipore or Applied Biosystems Inc.

Trityl (Trt), and/or t-butyl (tBu) were utilized as protecting groups for the Cys residues. The Fmoc group was used for amino protection during the coupling procedure.

Primary amine protection on amino acids was achieved with Fmoc and side chain protection groups were t-butyl for serine, tyrosine, aspartic acid, glutamic acid, and threonine; Pmc (2,2,5,7,8-pentamethylchroma sulfonate) for arginine; N-t-butyloxycarbonyl for tryptophan, and lysine; and N-trityl for histidine, asparagine, and glutamine. Side chain protecting groups are not shown in the figures below for convenience.

Removal of the peptides from the resin and simultaneous deprotection of the side chain functions were achieved by treatment with reagent K (5% water, 5% phenol, 5% thioanisole, 2.5% 1,2-ethanedithiol, and 82.5% trifluoroacetic acid) or slight modifications of it. Alternatively, in the synthesis of those peptides, with an amidated carboxyl terminus, the fully assembled peptide was cleaved with a mixture of 90% trifluoroacetic acid, 5% ethanedithiol, and 5% water, initially at 4 C, and gradually increasing to room temperature.

The deprotected peptides were precipitated with diethyl ether.

In all cases, purification was by preparative, reverse-phase, high performance liquid chromatography on a C, 8 bonded silica gel column with a gradient of acetonitrile/water in 0.1% trifluoroacetic acid. The homogeneous peptides were characterized by MALDI/MS or electrospray mass spectrometry and amino acid analysis when applicable.

EXAMPLE 2

Dimer Synthesis: Regioselective Cysteine Pairing

This technique calls for the use of two different Cys protecting groups. The first disulfide bond is formed by selectively removing the first set of protecting groups. The second disulfide bond is formed by removing the second set of protecting groups from the peptide as shown schematically below.

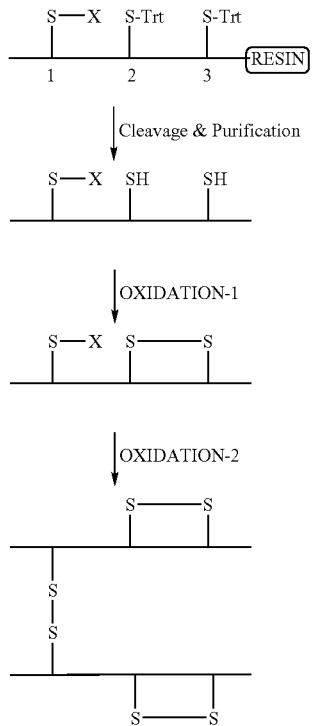

Regioselective Cysteine Pairing-Peptides Containing Tryptophan

As shown below, Acm was used as the protecting group for the first Cys and Trt was used for the second and third Cys residues. The procedure of Tamamura et al., Chem. Commun. 151 (1998) was used to effect the dimerization. The linear purified peptide (with 1-S-S- and 1-Acm) (80 mg, 0.043 millimole) and silver trifluoromethanesulfonate (1.09 gm, 100 equiv.) is dissolved in TFA-anisole mixture (160 ml at 20:1 v/v) to give a concentration of 2 mg of peptide in 1ml of TFA-anisole.

The reaction mixture is stirred for three hours at room temperature and filtered into cold ether. The precipitate is further washed three times with cold ether. Then the dried crude peptide is suspended in DMSO-1 M HCl (80:20 v/v). The concentration is 2.5 mg/1ml solution. After stirring overnight, the peptide is further purified by RP-HPLC.

The fractions are collected and further analyzed by analytical HPLC. The pure fractions are pooled together, lyophilized and characterized by MS. The overall yield is 12% by weight.

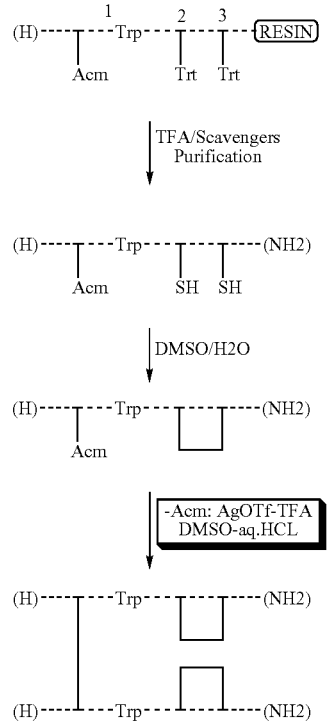

Regioselective Cysteine Pairing-Peptides Containing other than Tryptophan

As shown below, tBu—was used as the protecting group for the first Cys; whereas, Trt was used for the second and third Cys residues. The procedure of Akaji et al., Tetrahedron Letters 33: 1073-1076 (1992) was utilized to effect the dimerization.

To the linear purified peptide with (1-S—S— and 1-tBu) (10 mg, 0.0053 millimole) is added diphenylsulfoxide (10.75 mg, 10 equiv.) and anisole (2 or 3 drops). The above mixture is dissolved in trifluoroacetic acid (3 ml). To this mixture is added, chlorotrimethylsilane (67.5 ml, 100 equiv.). The solution is stirred for 90 minutes at room temperature. The reaction mixture is filtered into cold ether and the precipitate is further washed three times. The crude peptide is further purified by RP-HPLC and checked by MS. The overall yield is 60% by weight.

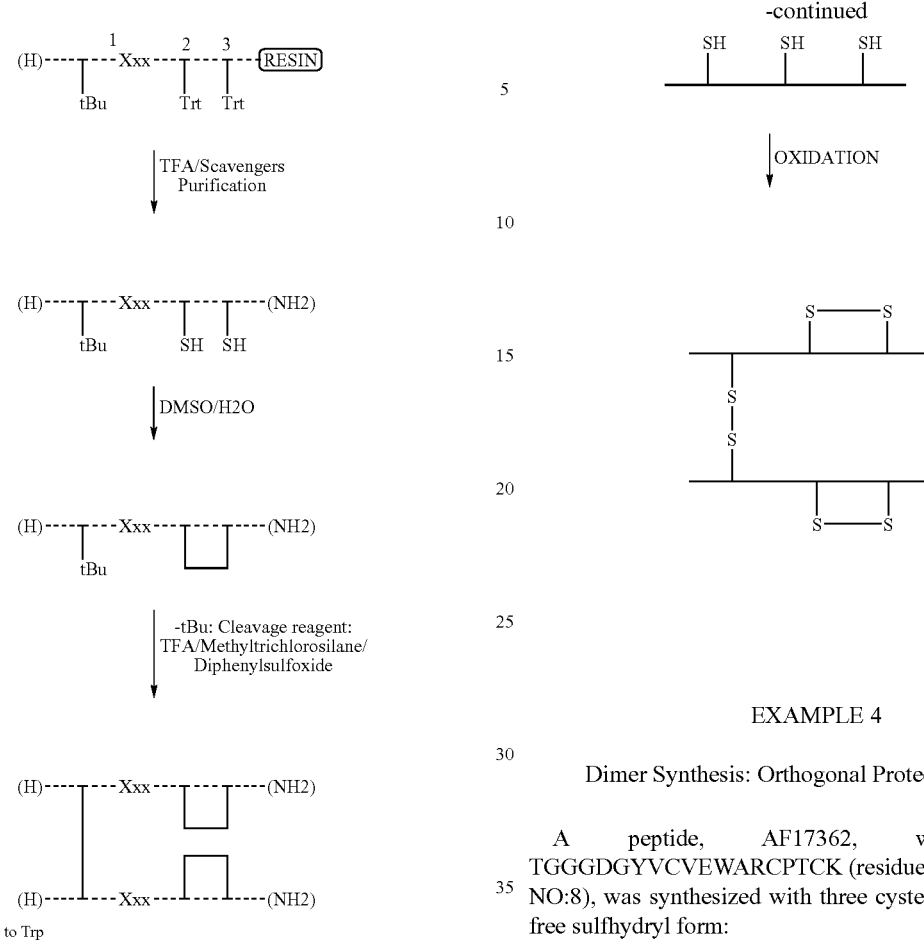

Xxx Not equal to Trp

EXAMPLE 3

Dimer Synthesis: Oxidative Folding of Cysteine

This technique is described further in Morder et al., Biopolymers (Peptide Science) 40: 207-234 (1996). Unlike the regioselective cysteine pairing method, only one type of protecting group for the cysteine was used. The linear peptide with 3-SH has been oxidized to form a dimer directly as described below.

The linear peptide with 3-SH is oxidized in Tris buffer, pH 7.8 for two days. The course of the reaction is monitored by HPLC. The product can be purified by RP-HPLC. After lyophilization, the stereochemistry is confirmed by strong cation exchange column chromatography and by mass spectrum. The disulfide bond pattern can be checked by tryptic digest.

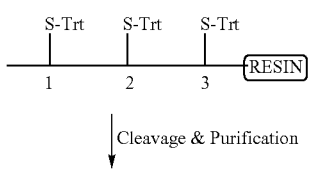

Cleavage & Purification

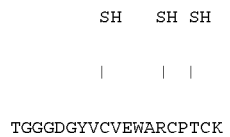

EXAMPLE 4

Dimer Synthesis: Orthogonal Protecting Groups

A peptide, AF17362, with sequence TGGGDGYVCVEWARCPTCK (residues 36-50 of SEQ ID NO:8), was synthesized with three cysteine residues in the free sulfhydryl form:

```
        SH    SH SH
        |     |  |
TGGGDGYVCVEWARCPTCK
```

(residues 32-50 of SEQ ID NO:8)

When AF17362 was dissolved in 50 mM Tris buffer, pH 7.8 and assayed immediately, it competed with $[_{125}I]$ IL-5 for binding to IL-5Ra ECD with an $IC_{50}$ of 120 nM. However, when the peptide solution was left at room temperature for 10 days the $IC_{50}$ in the binding assay dropped to 550 pM. Concomitant with this change in binding affinity, the peptide's retention time by C 8 RP-HPLC shifted (but remained a single peak), and mass spectroscopic (MS) analysis revealed that the peptide had spontaneously formed a disulfidelinked dimer.

To determine the disulfide pattern of the peptide, the dimeric form of AF17362 was digested with trypsin and analyzed by LC-electrospray-MS and MALDI-MS. The MS analysis of the tryptic digest revealed fragments consistent with the presence of a single symmetrical dimer structure containing an interchain disulfide bond between the cysteines in position 9 and intrachain disulfide bonds between the cysteines in positions 15 and 18 on each chain:

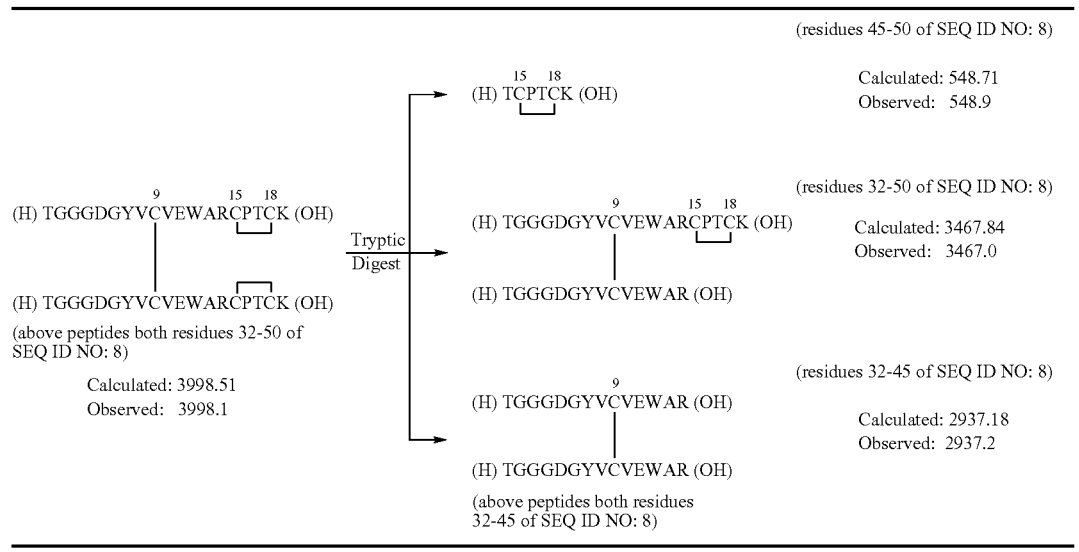

The presence of a turn-inducing proline residue at position 16 would seem likely to favor the formation of such a $C_{15}$-$C_{18}$ disulfide bond above other possible combinations, and kinetic analysis of the dimerization process by nuclear magnetic resonance spectroscopy confirmed the formation of this intramolecular bond prior to intermolecular dimerization.

A dimer peptide was prepared synthetically using orthogonal protecting groups.

Synthesis was performed on HMP resin using an ABI peptide synthesizer 431A or 433A and Fmoc-chemistry. Each step was double coupled using HBTU/HOBt reagent. The acetamidomethyl (Acm-) protecting group was used for the Cys in position 9 and trityl (Trt) for the Cys in positions 15 and 18. Other protecting groups were tBu—for Thr and Tyr, —OtBu for Asp and Glu, Boc—for Trp and Pmc—for Arg. After the final coupling, the Nterminal Fmoc-group was removed. The peptide was cleaved and deprotected from the resin with TFA-DCM-anisole-2 mercaptoethanol (89.7%-10%-0.1%-0.2%). The crude peptide was further purified by C18 RP-HPLC. The peptide was oxidized overnight in 30% DMSO-water at 1 mg/ml to form the intrachain disulfide bond [J. P. Tam, C.-R. Wu, W. Liu, J.-W. Zhang, J Am. Chem. Soc. 113: 6657 (1991)]. The interchain disulfide bond was formed by using AgOTf-TFA followed by DMSO-aq. HCl (Tamura et al., Chem. Commun. 1: 151 (1998)). The product was purified by C, 8 RP-HPLC and confirmed by ESMS and MALDI/MS. The resulting peptide, AF 18748,

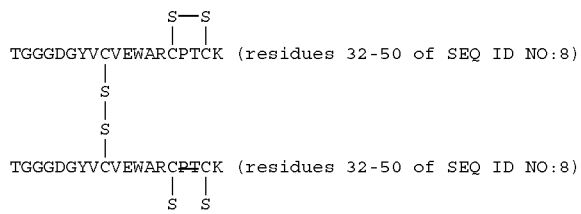

was indistinguishable from the dimeric form of AF 17362 by all criteria tested (RP-HPLC, capillary electrophoresis, and tryptic digest) and competed with [$_{125}$I] IL-5 for binding to IL5Ra ECD with essentially the same potency (IC50 of 780 pM).

The ability of AF1 8748 to bind to the native IL-SR a/(3 complex on TF-1 cells was assessed in a competition binding assay (as described in McKinnon et al., J. Exp. Med. 186: 121 (1997)). The binding of [$_{125}$I] IL-5 to TF-1 cells was inhibited by either unlabeled IL-5 ($IC_{50}$ 310 20 pM) or AF 18748 (IC50 400 40 pM), demonstrating that AF 18748 can potently block IL-5 binding to the native heterodimeric form of the receptor, exhibiting an affinity similar to the natural ligand (FIG. 1).

Figure 2:
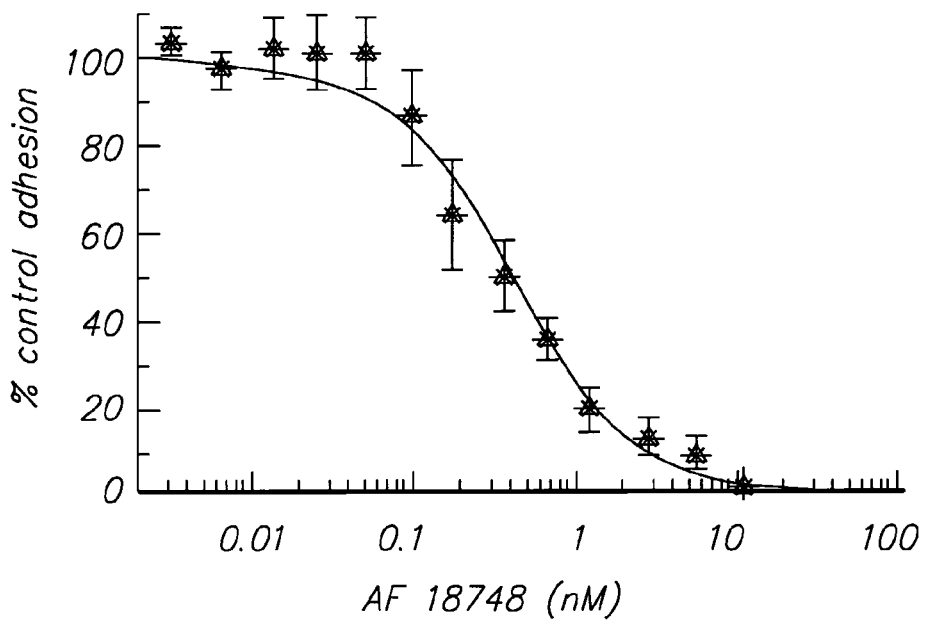
FIG. 2 shows the results of a functional binding experiment demonstrating inhibition of IL-5-induced eosinophil adhesion by AF 18748.
Figure 3:
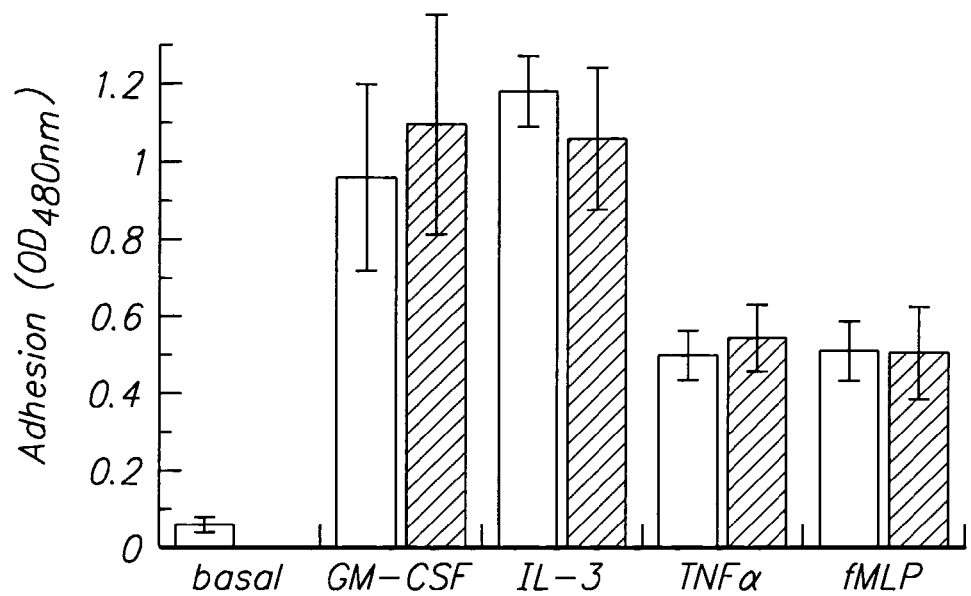
FIG. 3 shows the specificity of action of AF 18748, which has no effect on eosinophil adhesion induced by GM-CSF, IL-3, TNFa or fMet-Leu-Phe.

The functional activity of AF 18748 was assessed in a human eosinophil adhesion assay (following the method of D. Fattah, et al, Cytokine 8: 248 (1996)). The peptide alone was devoid of agonist activity, but completely inhibited IL-5 induced eosinophil adhesion to immobilized IgG with an IC50 of 348 67 pM (FIG. 2). Furthermore, concentrations of AF18748 up to I, uM had no effect on eosinophil adhesion induced by the related cytokines GM-CSF and IL-3, the unrelated cytokine TNFa or the chemotactic peptide fMet-Leu-Phe (FIG. 3). AF18748 is therefore a potent and selective antagonist of IL-5 in a human eosinophil functional assay.

EXAMPLE 5

Bioassays

Bioactivity of synthetic peptides and MBP-peptide fusions is measured using a Cytosensor microphysiometer (Molecular Devices) to record the metabolic response of TF-1 cells (a human leukemia cell line) to IL-5 in the presence or absence of peptide. After overnight incubation without IL-5, these cells exhibited a robust increase in metabolic activity when IL-5 is added to the medium. This increase was measured by the microphysiometer as an increase in the rate of acidification of weakly buffered tissue culture medium.

TF-1 cells were seeded into microphysiometer chambers at a density of 1.5×105 cells/chamber and grown overnight in DMEM tissue culture medium containing 10% fetal bovine serum, but lacking the 1 ng/ml IL-5 (R & D Systems) that is required for long-term maintenance of these cells in culture. The chambers were then placed in the microphysiometer and incubated with weakly buffered DMEM/F12 medium containing 1% human serum albumin until a baseline rate of medium acidification was established.

Varying dilutions of test peptide were then introduced for 15 min. None of the peptides tested had any effect on the baseline acidification rate. IL-5 at 10 ng/ml was then introduced for 25 minutes in the continued presence of test peptide. The chambers were then flushed with fresh medium.

Typically, maximal response to IL-5 occurred within 20 min. of the onset of IL-5 addition to the medium. In the absence of test peptide this response was typically a 1.5 to 2-fold increase in the rate of medium acidification. All peptides tested were able to reduce or completely block the response of the TF-1 cells to IL-5. Other, randomly chosen control peptides, at the same or higher concentrations, had no effect. The test peptides also had no effect on the robust microphysiometer response of TF-1 cells to TNFa, indicating that the test peptides were exhibiting their effect by specifically antagonizing IL-5 action. The $IC_{50}$ for test peptides was defined as that peptide concentration which gave a 50% reduction in the maximal IL-5 response when compared to the response to IL-5 alone.

EXAMPLE 6

Binding Affinity

Binding affinities of synthetic peptides for IL-5Ra were measured in a competition binding assay using radio-iodinated IL-5. Immulon 4 (Dynatech) microtiter wells were coated with streptavidin (Sigma) by incubating 100 ul of a 50 ug/ml solution in PBS for 30 min. at 37. The wells were blocked with 200 ul of 1% BSA in PBS for 15 min. at 37, followed by 100 III of biotinylated monoclonal antibody, designated mAb 179, at 5 u. g/ml in PBS. Soluble IL-5Ra was then immobilized in the wells by incubating 100 pi of a solution of soluble receptor harvest diluted 1: 5000 in PBS/0.1% BSA for 1 hr. at 4. After washing away unbound receptor, 50 ul of various concentrations of test peptide diluted in PBS/0.1% BSA were added to the wells, followed by 50 pl of a fixed concentration of [$_{125}$I] IL-5 (Amersham). The binding reactions were incubated at 4 C for 2 hr, then washed with PBS to remove unbound [$_{125}$I] IL-5. Bound [$_{125}$I] IL-5 was determined by gamma counting.

Total binding was defined by the amount of [$_{125}$I] IL-5 bound in the absence of any competitor. Non-specific binding was defined by the amount of [$_{125}$I] IL-5 bound in the presence of 30 nM IL-5. Peptide binding data was analyzed to determine the peptide concentration required to reduce specific [$_{125}$I] IL-5 binding by 50% (IQo)-Under the conditions described the IC50 values determined should be similar to the dissociation constant (Kd) of the peptides for IL-5Ra.

EXAMPLE 7

Scintillation Proximity Binding Assay

Binding affinities of synthetic peptides for IL-5Ra were measured in a scintillation proximity assay (SPA) using radio-iodinated IL-5. Streptavidin coated SPA beads (Amersham) were suspended in IL-5 binding buffer (phosphate buffered saline, 0.1% bovine serum albumin, 0.2% NaN3) at 2 mg beads/ml of buffer. Biotinylated mAb 179 was adsorbed onto the beads at a ratio of 2 ig Ab/mg beads by incubating the beads and antibody with agitation for at least 2 h. at 4. The beads were pelleted at 2500 rpm and resuspended at 2 mg/ml in binding buffer. Soluble IL-5Ra was then adsorbed onto the beads by diluting a solution of soluble receptor harvest 1:500 into the bead suspension and incubating with agitation for 2 hr at 4. The beads were again pelleted at 2500 rpm and resuspended at 2 mg/ml in binding buffer. Competition binding assays were carried out in 100p1 reactions in white polystyrene microtiter plates. These reactions contained 0.05 mg of receptor coated SPA beads, various concentrations of test peptide diluted in binding buffer, and 20 pM [$_{125}$I] IL-5 (Amersham). The plates were incubated at room temperature for 1 hour with agitation, then centrifuged for 5 min at 1500 rpm followed by scintillation counting on a Topcount instrument (Packard). Total binding was defined by the amount of [$_{125}$I] IL-5 bound in the absence of any competitor. Non-specific binding was defined by the amount of [$_{125}$I] IL-5 bound in the presence of 30 nM IL-5. Peptide binding data was analyzed to determine the peptide concentration required to reduce specific [$_{125}$I] IL-5 binding by 50% ($IC_{50}$). Results for dimers of the following monomeric structures are provided below. In each instance, the dimer has both intramolecular and intermolecular disulfide linkages as shown generically below:

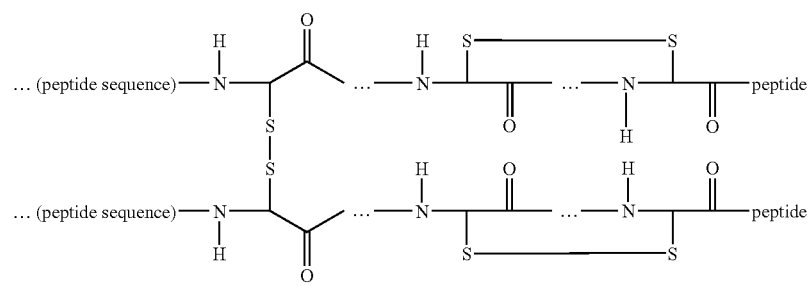

The results are presented as "pIC$_{50}$" which represents the negative log of the molar IC$_{50}$.

| SEQ ID NO: | Monomer Structure | SPA pIC$_{50}$ | Micro-physiometer pIC$_{50}$ |
|---|---|---|---|
| residues 32-50 of SEQ ID NO:8 | (H)-TGGGDGYVCVEWARCPTCK-(OH) | 9.1 | 9.6 |
| residues 36-50 of SEQ ID NO:11 | (H)-EGYVCVEWARCPTCK-(OH) | 8.7 | 9.2 |
| residues 36-50 of SEQ ID NO:12 | (H)-EGYVCVEWARCPTCR-(OH) | 8.4 | 9.6 |
| residues 36-50 of SEQ ID NO:14 | (H)-EGYVCVEFARCPTCR-(OH) | 6.8 | N.D. |
| residues 36-50 of SEQ ID NO:14 | (H)-EGYVCVEFARCPTCR-(NH$_2$) | 6.4 | N.D. |
| residues 37-50 of SEQ ID NO:17 | (H)-GYVCVEFARCPTCG-(NH$_2$) | 6.1 | N.D. |
| residues 36-50 of SEQ ID NO:13 | (H)-EGYVCVEFARCPTCG-(NH$_2$) | 6.6 | N.D. |
| residues 36-50 of SEQ ID NO:18 | (H)-GYVCVEWARCPTCR-(OH) | 8.2 | 8.4 |
| residues 36-50 of SEQ ID NO:12 | (H)-EGYVCVEWARCPTCR-(NH$_2$) | 8.1 | 9.1 |
| residues 36-50 of SEQ ID NO:15 | (H)-EGYVCVEWARCPTCG-(NH$_2$) | N.D. | 9.1 |
| residues 36-50 of SEQ ID NO:12 | (Ac)-EGYVCVEWARCPTCR-(NH$_2$) | N.D. | 9.1 |
| residues 36-50 of SEQ ID NO:11 | (Ac)-EGYVCVEWARCPTCK-(NH$_2$) | N.D. | 8.4 |
| residues 36-50 of SEQ ID NO:12 | (Ahx)-EGYVCVEWARCPTCR-(NH$_2$) | N.D. | 9.0 |
| residues 36-50 of SEQ ID NO:10 | (Ac)-EGYVCVEWAACPTCR-(NH$_2$) | N.D. | 6.9 |

Results for an alternative representative dimer are provided below.

| SEQ ID NO: | Structure | SPA pIC$_{50}$ | Micro-physio-meter pIC$_{50}$ |
|---|---|---|---|
| residues 36-50 of SEQ ID NO: 9 | (Ac)EGYV(Dpr)VEWARCPTCR(NH$_2$)<br>              \|<br>              NH<br>                \\<br>                  C=O<br>                /<br>              NH<br>              \|<br>residues 36-50 of SEQ ID NO: 99   (Ac)EGYV(Dpr)VEWARCPTCR(NH$_2$) | N.D. | 6.5 |

EXAMPLE 8

Biometric Imaging Assay

A "sandwich" binding assay using microvolume fluorimetry (Martens et al., Anal. Biochem., 273: 20 (1999)) was used to measure the ligand dependent association of two receptor proteins. IL-5RaECD (the extracellular domain (ECD) of the human IL-5 receptor a chain) was immobilized onto 10, um beads and incubated with soluble, fluorescently labeled IL-5Ra ECD in the presence or absence of IL-5 or peptide.

Fluorescently labeled mAbl79 was prepared using Cy5 monofunctional reactive dye (Amersham) according to the manufacturer's instructions. (As disclosed in Martens et al., supra, Cy5.5 dye is also suitable.) Fluorescent mAbl79: IL-5Ra ECD complexes were formed by preincubating the labeled antibody with an equimolar amount of receptor ECD in phosphate buffered saline (PBS) for 1 hr at room temperature. Mono A 10 um polystyrene beads (Pharmacia) were coated first with biotinylated bovine serum albumin, then sequentially with streptavidin, biotinylated mAbl79, and IL-5Ra ECD. The receptor coated beads were incubated in 100 pl PBS containing 1 % BSA, 0.02 % sodium azide, and 0.05% Tween-20, 5nM labeled mAbl79: IL-5Ra ECD complex and serial dilutions of human IL-5, AF 18748 (a dimer of residues 32-50 of SEQ ID NO: 8), or AF 17121, a peptide monomer with the sequence VDECWRIIASHTWFCAEE (residues 33-50 of SEQ ID NO: 19) with intramolecular disulfide linkages:

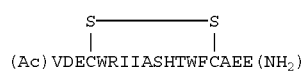

(Ac) VDECWRIIASHTWFCAEE (NH$_2$)

Figure 4:
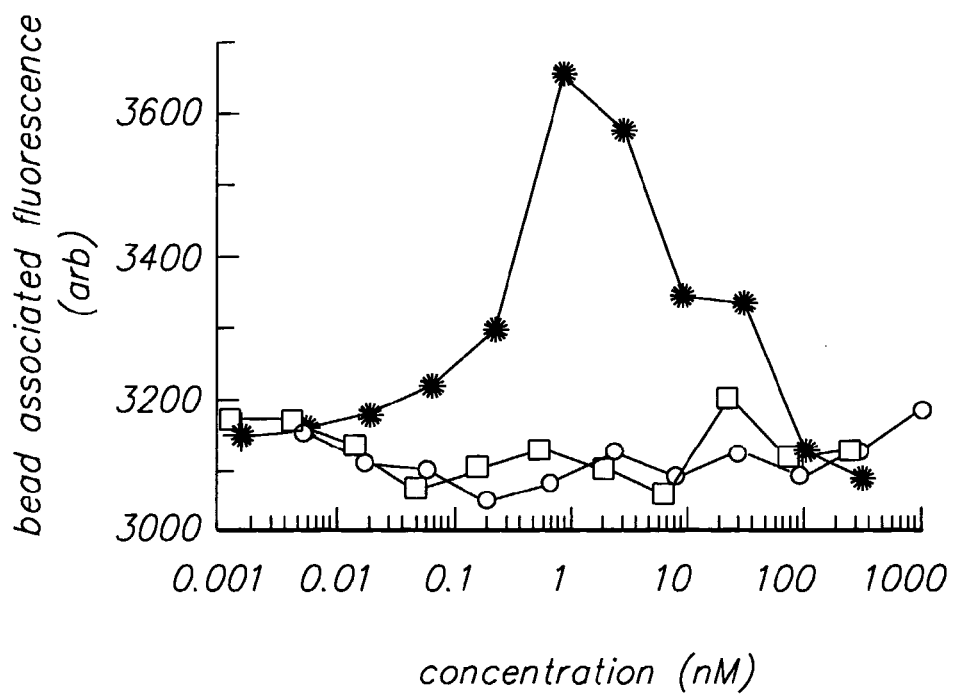
FIG. 4 shows fluorescence as a function of the concentration of AF 18748 (closed circles), AF 17121 (open circles) or human IL-5 (open squares) added to microtiter plates containing IL-5RaECD-coated beads.

As shown in FIG. 4, fluorescently labeled IL-5Ra ECD was incubated with IL-SRaECDcoated polystyrene beads and serial dilutions of AF 18748 (open circles), AF 17121 (closed circles), or human IL-5 (open squares). The binding reactions were incubated in microtiter plates overnight at room temperature, then microvolume fluorimetry measurements of beadassociated fluorescence were made using an FMAT instrument (Perkin-Elmer). The data points represent averages of triplicate determinations from a single representative experiment, providing biochemical evidence of AF 18748-induced IL-5-a dimerization.

Addition of increasing amounts of AF 18748 over a range from 10 pM to 1 nM caused an increase in the association of the fluorescently labeled receptor to the beads (FIG. 4), indicating that the peptide is binding simultaneously to both an immobilized receptor and a soluble receptor. At concentrations of AF 18748 greater than 1 nM the binding of labeled receptor to the beads decreases, presumably due to the excess of peptide favoring a 1:1 association of peptide with both immobilized and soluble receptor. Addition of the monomeric IL-5 antagonist peptide, AF 17121, did not mediate the association of labeled receptor with the beads (FIG. 4), demonstrating monovalent receptor binding.

Moreover, although IL-5 is a disulfide linked homodimer it also did not mediate receptor association. This is consistent with previous reports demonstrating that each IL-5 dimer binds to a single IL-5Ra ECD in solution (R. Devos, et al, Journal Of Biological Chemistry 268: 6581 (1993); K. Johanson, et al, J. Biol. Chem. 270: 9459 (1995)).

Figure 5:
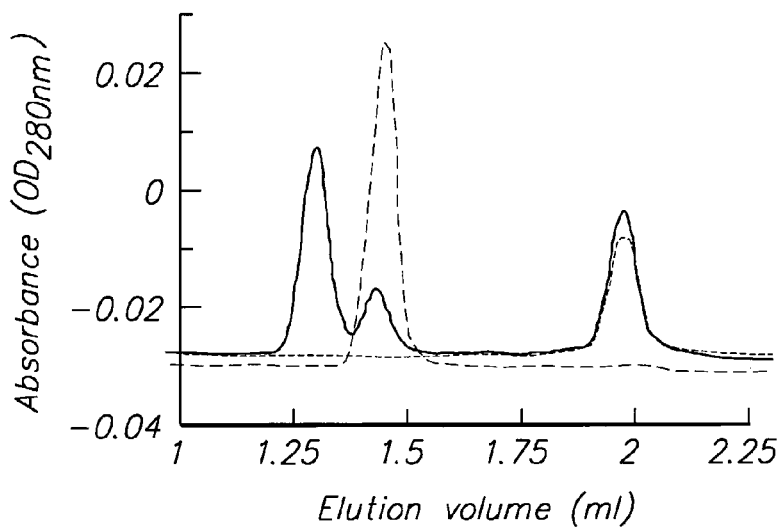
FIG. 5 shows a gel filtration chromatograph where IL-5Ra-ECD (dashed line), IL5RaECD plus AF 17121 (dotted line) or IL-5RaECD plus AF 18748 (solid line).

Secondly, the ability of peptides to induce receptor dimerization was studied using gel filtration chromatography. Gel filtration chromatography was performed on a Pharmacia Smart system using a Precision Superdex 200 3. 2/30 column at 25 C with a flow rate of 10 pl/min. The buffer was 50 mM Tris pH 7.5, 0.5 M NaCl. The column was calibrated using the Biorad Gel filtration molecular weight standards which contain Thyroglobulin, 670 KD; Bovine gamma globulin, 158 KD; Chicken albumin, 44 KD; equine myoglobin, 17 KD; Vitamin B12, 1.35 KD. As shown in FIG. 5, IL-5Ra ECD was loaded onto the column alone (dashed line) or in the presence of equimolar amounts of AF 17121 (dotted line) or AF 18748 (solid line). Elution volumes and calculated molecular weights are given in Table 3. Results shown are from a single experiment, representative of three separate runs for each condition.

Soluble IL-5Ra ECD appeared as a single peak with a calculated molecular weight of 89.5 kDa (FIG. 5). Although this is considerably higher than predicted, the monomeric nature of the soluble receptor was confirmed by comparing its behavior under native and denaturing (6M guanidine hydrochloride) conditions. The IL-5Ra is extensively glycosylated, and this is probably the source of the discrepancy in molecular weight.

The effect of peptide monomer AF 17121 was compared to the effect of the dimer AF 18748. The presence of AF 17121 had no effect on the elution of the receptor (FIG. 5).

In contrast, the apparent size of the IL-5Ra ECD increased dramatically in the presence of AF18748, consistent with a change from a monomeric to a dimeric form (FIG. 5, Table 3).

Thirdly, analytical ultracentrifugation was used to examine the stoichiometry of the AF18748: IL-5Ra ECD interaction. Velocity sedimentation experiments were conducted on a Beckman XLI Ultracentrifuge equipped with absorption and interference optics and an An60Ti rotor. The experiments were run at 40,000 rpm in charcoal-filled Epon double sector centerpieces and the data was collected at 280 nm as single scans at a spacing of 0.01 cm in continuous scan mode. The temperature was held at 25 C and the buffer was 50 mM Tris pH 7.5, 0.5 M NaCl. For experiments with peptide, equal amounts were added to both reference and sample compartments. Data was analyzed using both Ultrascan (Borroes Demeler) and DCDT (Walter Stafford). Data shown is from a single experiment representative of two others.

Figure 6:
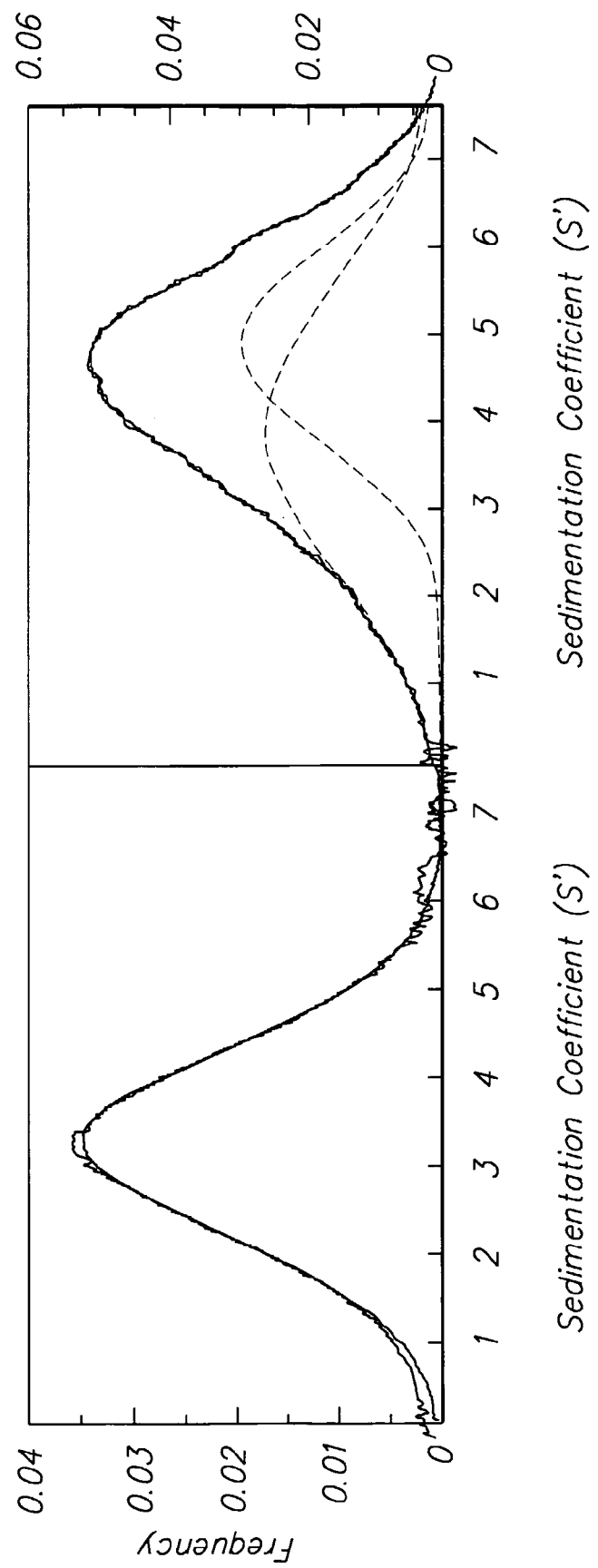
FIG. 6 shows the results of velocity sedimentation experiments with IL-5RaECD (3.3S) and IL-5RaECD in the presence of AF 18748: another peak appears at 5.1 S indicating dimerization.

Analysis of data collected in velocity sedimentation experiments with the IL-5Ra ECD revealed a Gaussian distribution of species centered at 3.3S (FIG. 6). Addition of a molar equivalent of AF 18748 resulted in a change in the shape of the distribution of species.

In the presence of a molar equivalent of AF18748, analysis of the data revealed the presence of two principal species, each with a Gaussian distribution, giving apparent sedimentation coefficient values of 3.2 S and 5.1 S. These results are entirely consistent with the result expected to be obtained with peptide-induced receptor dimerization (FIG. 6).

TABLE 3

|   | Elution Volume | Calculated MW | Receptor State |
| --- | --- | --- | --- |
| AF17121 alone | 2.020 | 2.5 | n.a. |
| AF18748 alone | 1.956 | 3.9 | n.a. |
| IL-5RαECD alone | 1.427 | 89.5 | Monomer |
| IL-5RαECD + AF17121 | 1.425 | 89.5 | Monomer |
|   | 2.020 | 2.5 |   |
| IL-5RαECD + AF18748 | 1.282 | 208.5 | Dimer |
|   | 1.425 | 89.5 | Monomer |
|   | 1.956 | 3.9 |   |

EXAMPLE 9

Chimeric IL-5Ra/EGFR Reporter Cell Assay

A system comprising a chimeric IL-5R-a/EGFR reported cell assay was designed to analyze receptor binding stoichiometry in a cellular context. A chimeric receptor consisting of the IL-5Ra ECD fused to the transmembrane spanning and intracellular domains of the epidermal growth factor receptor (EGFR) was constructed, and stably expressed in Ba/F3 cells that also contained a luciferase reporter gene under the transcriptional control of the c-fos enhancer and minimal thymidine kinase promoter.

In the assay, Ba/F3 cells expressing a chimeric IL-5Ra/EGFR receptor and containing a luciferase reporter gene were starved overnight of the WEHI conditioned medium in which they were maintained, then seeded into microtiter wells at a density of 105 cells/well. Following stimulation, the cells were incubated for 4 hr at 37 in a 5% CO2 incubator. LucLite reagent (Packard) was then added to the wells according to the manufacturer's instructions and the plates were assayed for luciferase activity by counting in a Topcount instrument (Packard). Data points represent mean i SEM for 3 separate experiments performed in triplicate. The data has been normalized to the stimulation induced by I, uM AF 18748 in each experiment. The experiments shown in FIG. 7, with cells treated with serial dilutions of AF 18748 (closed circles), AF 17121 (open circles) or IL5 (open squares), demonstrate that AF18748 activates the IL-5Ra/EGFR chimeric receptor.

Figure 7:
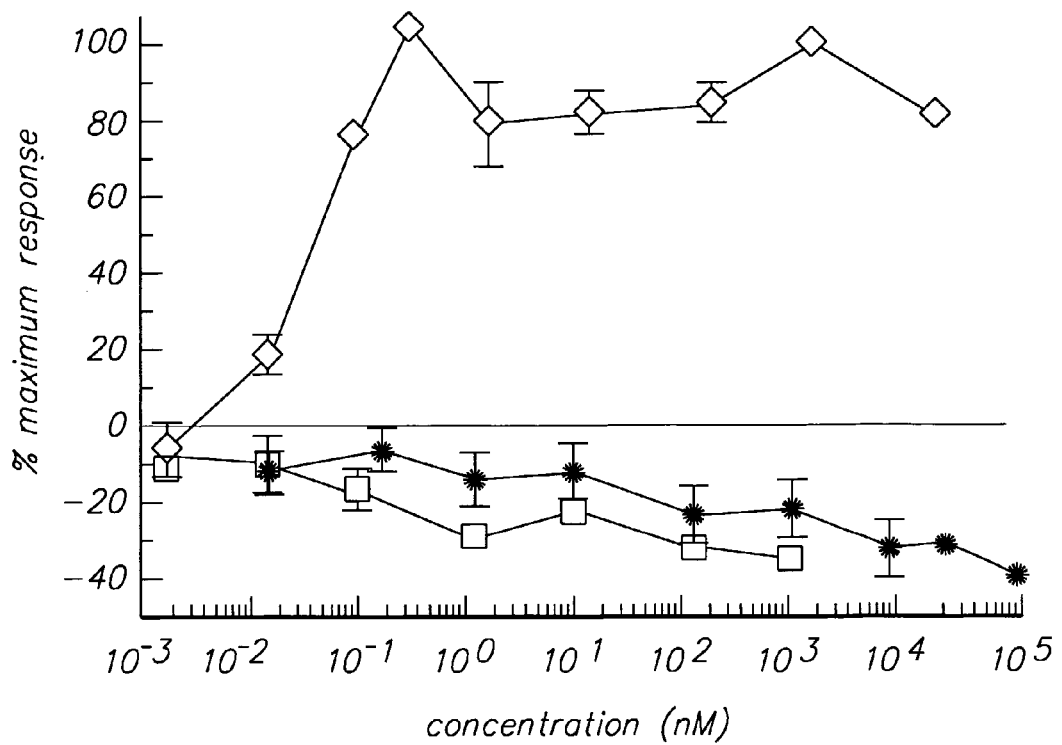
FIG. 7 shows the response of cells expressing chimeric IL-5Ra/EGFR treated with AF 18748 (open circles), AF 17121 (closed circles) or IL-5 (open squares).

Since activation of native EGFR by ligand-induced homodimerization results in an increase in c-fos transcription (Hazzalin et al., Oncogene 15: 2321 (1997)), homodimerization of the IL-5Ra/EGFR chimera should likewise induce expression of the luciferase transgene. Stimulation of Ba/F3 cells expressing the chimera with AF 18748 resulted in a dose dependent increase in luciferase activity while the monovalent ligands IL5 or AF 17121 had no effect (FIG. 7).

Furthermore, activation of the luciferase reporter by AF 18748 was antagonized by IL-5 (FIG. 8), demonstrating that this is a specific IL-5-receptor mediated event. In these experiments, cells were treated with 200 pM AF18748 in the presence of increasing concentrations of IL-5. Data points represent the average of triplicate determinations from a single representative experiment, and demonstrate that IL-5 inhibits the AF18748-induced activation of the chimeric IL-5Ra/EGFR in this reporter cell assay.

This also demonstrates that the monovalent nature of the IL-5:IL-5Ra interaction observed in solution (Devos et al., J.

Figure 8:
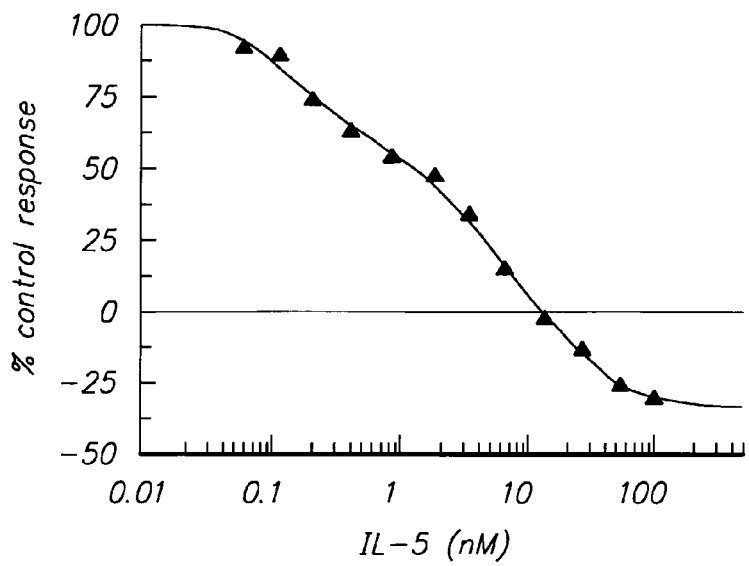
FIG. 8 shows the response of cells expressing chimeric IL-5Ra/EGFR treated with 200 pM AF18748 in the presence of increasing amounts of IL-5.

Biol. Chem 268: 6851 (1993); K. Johanson et al., J. Biol. Chem. 270: 9459 (1995)) is maintained when the receptors are anchored in a cell membrane. Treatment of unstimulated cells with IL-5 or AF 17121 actually reduced basal level of luciferase expression (FIG. 7), and IL-5 reduced the AF18748 stimulated level to well below control levels (FIG. 8). This suggests that there is some degree of ligand independent receptor dimerization due to overexpression, that can be inhibited by the binding of a monovalent ligand.

This combination of biochemical, biophysical and cell-based data shows that AF18748 can bind to two IL-5Ra chains simultaneously. In contrast to the receptors for EPO and TPO where ligand induced receptor homodimerization is required for activation, activation of the IL-5 receptor involves the heterodimerization of the ligand binding a-chain with the pc signaling chain. Thus, while the dimeric nature of the peptides that bind to the EPO and TPO receptors underpins their agonist activity, the ability to occupy two IL-5 receptor a-chains leads to the high potency functional antagonism exhibited by AF 18748. The multivalent binding of the dimer peptide will sequester a-chains and thereby prevent the ligand-induced receptor heterodimerization required to initiate signal transduction.

EXAMPLE 10

In Vivo Serum Stability

Figure 9:
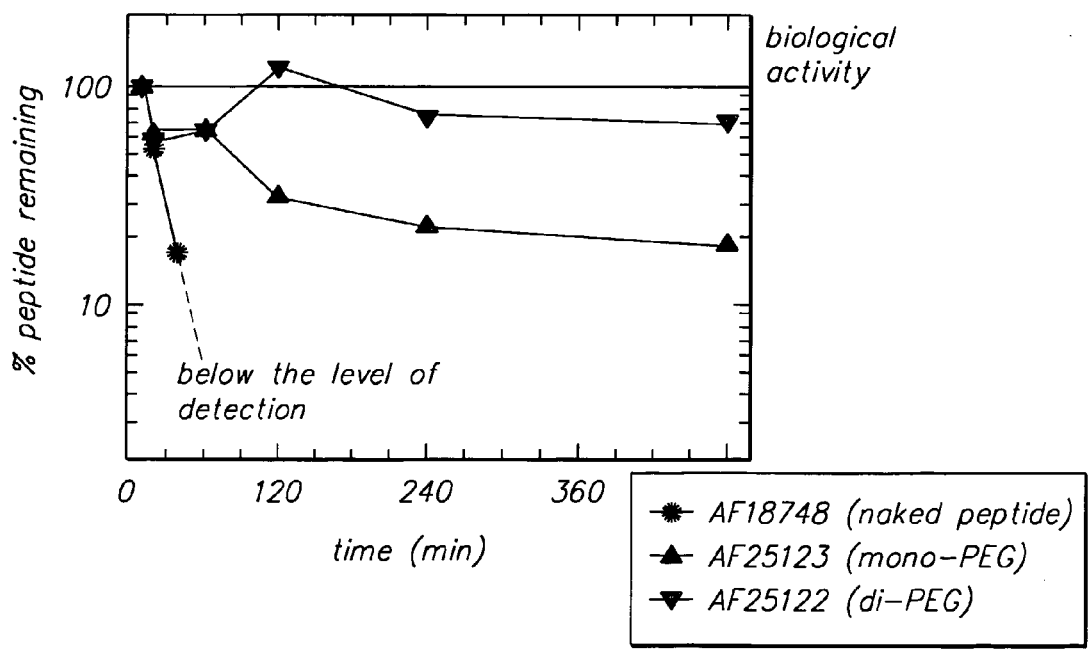
FIG. 9 shows the stability of AF18748 (closed circles), AF25123 (closed upwardpointing triangles) and AF25122 (closed downward-pointing triangles) in vivo.

The length of time that peptide dimers remain in circulation was measured by injection of peptides into mice and subsequently measuring the amount of peptide remaining in circulation at various times after injection. As illustrated in FIG. 9, three peptide dimers with the same peptide sequence but differing in the amount of PEGylation were investigated. The compounds used were dimers comprising the peptide sequence SEQ ID NO: 8; the peptide dimer AF 18748 (lacking PEG), the mono-PEGylated peptide dimmer AF25123, and the diPEGylated peptide dimer AF25122, where PEGylation was with 20 kDa PEG linked to the N-terminus of one or both peptides of a dimer.

Peptides were dissolved at 0.125 mM (AF18748) or 0.5 mM (AF25122, AF25123) in 0.9% (w/v) saline and dosed into individual female CD-1 mice (about 25 g) via a lateral tail vein (100 microliter injection). At indicated times, shown in FIG. 9, terminal blood samples (2 animals per timepoint) were collected, by cardiac puncture, into heparinized tubes and centrifuged to yield plasma which was stored frozen. Peptides were extracted from the plasma by the addition of an equal volume of ice-cold acetonitrile and, following centrifugation, the supernatants containing the peptides were dried down and stored at 4 C.

The amount of peptide present in the serum extracts was evaluated by surface plasmon resonance techniques using a competition binding assay format on a BlAcore 1000 machine (Biacore AB, Uppsala, Sweden). A disulfide-linked dimer peptide of the sequence EGYVCVEWARCPTCK (residues 36-50 of SEQ ID NO: 11) was chemically coupled onto a CM-5 Biosensor chip using the manufacturer's standard protocol. Purified recombinant IL-5 receptor alpha chain extracellular domain was passed over the peptide coated chip and the binding of the IL-5 receptor to the EGYVCVEWARCPTCK (residues 36-50 of SEQ ID NO: 11) peptide dimer was monitored. The binding of IL-5 receptor alpha extracellular domain to the peptide coated surface could be inhibited in a dose dependent manner by each of the IL-5 antagonist peptides in solution. Thus the amount of inhibitory activity present in the serum extracts can be compared to a standard curve of known amounts of the same peptide to allow an accurate determination of the amount of peptide in the blood.

The invention claimed is:

1. A method for treating a patient having a condition mediated by IL-5 comprising administering to the patient a therapeutically effective amount of a compound that effects homodimerization of the alpha chain of the IL-5 receptor, wherein said compound comprises a member selected from the group of peptides consisting of:

```
TGGGDGYV X₃VE X₄ ARCPTCK;
(residues 32-50 of SEQ ID NO:1)

EGYV X₃VE X₄ ARCPTCK;
(residues 36-50 of SEQ ID NO:2)

EGYV X₃VE X₄ ARCPTCR;
(residues 36-50 of SEQ ID NO:3)

GYV X₃VE X₄ ARCPTCG;
(residues 36-50 of SEQ ID NO:4)

EGYV X₃VE X₄ ARCPTCG;
(residues 36-50 of SEQ ID NO:5)

GYV X₃VE X₄ ARCPTCR;
(residues 37-50 of SEQ ID NO:6)

and

EGYV X₃VE X₄ AACPTCR
(residues 36-50 of SEQ ID NO:7)
``` wherein $X_3$ is Cys, Lys, or Dpr, and $X_4$ is Nal, Trp, or Phe.

2. The method of claim 1, wherein the sequence is fourteen to fifty amino acid residues in length.

3. The method of claim 1, wherein the sequence is fourteen to twenty amino acid residues in length.

4. A method of claim 1, wherein the N-terminus of said peptide is selected from the group consisting of
—NRR₁, —NRC(O)R, —NRC (O)OR, —NRS (O)₂R, —NHC(O)NHR, succinimide, benzyloxycarbonyl-NH—, and benzyloxycarbonyl-NH-having from 1 to 3 substituents on the phenyl ring of said benzyloxycarbonyl-NH—, said benzyloxycarbonyl-NH-substituents selected from the group consisting of lower alkyl, lower alkoxy, chloro, and bromo, where R and R, are independently selected from the group consisting of hydrogen and lower alkyl,
wherein the C-terminus of said peptide has the formula-C (O)R₂ where R₂ is selected from the group consisting of hydroxy, lower alkoxy, and-NR₃R₄ wherein R₃ and R₄ are independently selected from the group consisting of hydrogen and lower alkyl and wherein the nitrogen atom of the-NR₃R₄ group can optionally be the amine group of the N-terminus of the peptide so as to form a cyclic peptide, and physiologically acceptable salts thereof.

5. The method of claim 1, wherein the compound binds to the interleukin 5 receptor (IL-5R) with an $IC_{50}$ of no more than about 2 mM as determined by a binding affinity assay.

6. The method claim 1, wherein the compound binds to the IL-5R with an IC50 of no more than about 100 uM as determined by a binding affinity assay.

7. The method of claim 1, wherein the compound comprises a sequence of amino acids selected from the groups consisting of

```
X₁-TGGGDGYVX₃VEX₄ARCPTCK-X₂;
(residues 32-50 of SEQ ID NO:1)

X₁-EGYVX₃VEX₄ARCPTCK-X₂;
(residues 36-50 of SEQ ID NO:2)

X₁-EGYVX₃VEX₄ARCPTCR-X₂;
(residues 36-50 of SEQ ID NO:3)

X₁-GYVX₃VEX₄ARCPTCG-X₂;
(residues 36-50 of SEQ ID NO:4)

X₁-EGYVX₃VEX₄ARCPTCG-X₂;
(residues 36-50 of SEQ ID NO:5)

X₁-GYVX₃VEX₄ARCPTCR-X₂;
(residues 37-50 of SEQ ID NO:6)

and

X₁-EGYVX₃VEX₄AACPTCR-X₂
(residues 36-50 of SEQ ID NO:7)
``` wherein $X_1$ is hydrogen or acyl; $X_2$ is $NH_2$ or —OH wherein —$NH_2$ indicates that the carboxy terminus of the compound has been amidated and —OH indicates that the carboxy terminus of the compound has not been derivatized.

8. The method of claim 1, wherein the compound further comprises an intramolecular disulfide linkage between two Cys residues.

9. The method of claim 1, wherein the compound further comprises a dimer with intermolecular disulfide, amide, carbamate, or urea linkages.

10. The method of claim 1 further comprising administering to said patient at least one other compound selected from the group consisting of β-adrenergic agonists, anticholinergics and anti-inflammatory corticosteroids.

11. The method of claim 1, wherein the compound is coupled to a polyethylene glycol molecule.

12. The method of claim 11, wherein the polyethylene glycol has an average molecular weight of between about 500 to about 100,000 daltons.

13. The method of claim 11, wherein the polyethylene glycol has an average molecular weight of between about 2,000 to about 40,000 daltons.

14. A method of claim 11, wherein the polyethylene glycol has an average molecular weight of between about 5,000 to about 20,000 daltons.

* * * * *

SEQUENCE LISTING

```
<160> NUMBER OF SEQ ID NOS: 19

<210> SEQ ID NO 1
<211> LENGTH: 81
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(31)
<223> OTHER INFORMATION: Variable amino acid; this range may encompass
      0 to 31 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(81)
<223> OTHER INFORMATION: Variable amino acid; this range may encompass
      0 to 31 amino acids with the proviso that total peptide length
      does not exceed 50 amino acids; see specification as filed for
      detailed description of R-groups, substitutions and preferred
      embodiments
<220> FEATURE:
```

```
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 1

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Thr
                20                  25                  30

Gly Gly Gly Asp Gly Tyr Val Xaa Val Glu Xaa Ala Arg Cys Pro Thr
            35                  40                  45

Cys Lys Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
 65                 70                  75                  80

Xaa

<210> SEQ ID NO 2
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 2

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
```

```
                  20                  25                  30

Xaa Xaa Xaa Glu Gly Tyr Val Xaa Val Glu Xaa Ala Arg Cys Pro Thr
            35                  40                  45

Cys Lys Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
                85

<210> SEQ ID NO 3
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 3

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Glu Gly Tyr Val Xaa Val Glu Xaa Ala Arg Cys Pro Thr
            35                  40                  45

Cys Arg Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
                85

<210> SEQ ID NO 4
<211> LENGTH: 86
```

```
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(36)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(86)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Gly Tyr Val Xaa Val Glu Xaa Ala Arg Cys Pro Thr
            35                  40                  45

Cys Gly Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa
                85

<210> SEQ ID NO 5
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
```

```
    embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 5

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Glu Gly Tyr Val Xaa Val Glu Xaa Ala Arg Cys Pro Thr
        35                  40                  45

Cys Gly Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
            85

<210> SEQ ID NO 6
<211> LENGTH: 86
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this paptide may exhibit internal disulfide
      bonding as well as dimerization
<220> FEATURE:
<221> NAME/KEY: MOD_RES
<222> LOCATION: (1)..(36)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(86)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
```

```
<220> FEATURE:
<223> OTHER INFORMATION: n-term may be acetylated
<220> FEATURE:
<223> OTHER INFORMATION: c-term may be amidatated

<400> SEQUENCE: 6

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Gly Tyr Val Xaa Val Glu Xaa Ala Arg Cys Pro Thr
         35                  40                  45

Cys Arg Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa
             85

<210> SEQ ID NO 7
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Cys, Lys or Dpr
<220> FEATURE:
<221> NAME/KEY: MOD_RES
<222> LOCATION: (43)
<223> OTHER INFORMATION: Nal, Trp or Phe
<220> FEATURE:
<223> OTHER INFORMATION: n-term may be acetylated
<220> FEATURE:
<223> OTHER INFORMATION: c-term may be amidatated

<400> SEQUENCE: 7

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Glu Gly Tyr Val Xaa Val Glu Xaa Ala Ala Cys Pro Thr
         35                  40                  45

Cys Arg Xaa Xaa Xaa Xaa Xaa Xaa Xaa Xaa Xaa Xaa Xaa Xaa Xaa
```

```
                50              55              60
Xaa Xaa Xaa Xaa Xaa Xaa Xaa Xaa Xaa Xaa Xaa Xaa Xaa Xaa Xaa Xaa
        65              70              75              80

Xaa Xaa Xaa Xaa Xaa
                85

<210> SEQ ID NO 8
<211> LENGTH: 81
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(31)
<223> OTHER INFORMATION: Variable amino acid; this range may encompass
      0 to 31 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(81)
<223> OTHER INFORMATION: Variable amino acid; this range may encompass
      0 to 31 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 8

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Thr
            20                  25                  30

Gly Gly Gly Asp Gly Tyr Val Cys Val Glu Trp Ala Arg Cys Pro Thr
            35                  40                  45

Cys Lys Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
        65                  70                  75              80

Xaa

<210> SEQ ID NO 9
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
```

```
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (40)
<223> OTHER INFORMATION: Dpr
<220> FEATURE:
<223> OTHER INFORMATION: n-term may be acetylated
<220> FEATURE:
<223> OTHER INFORMATION: c-term may be amidatated

<400> SEQUENCE: 9

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
             20                  25                  30

Xaa Xaa Xaa Glu Gly Tyr Val Xaa Val Glu Trp Ala Arg Cys Pro Thr
         35                  40                  45

Cys Arg Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
             85

<210> SEQ ID NO 10
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
```

<223> OTHER INFORMATION: Variable amino acid; this range may encompass
     0 to 35 amino acids with the proviso that total peptide length
     does not exceed 50 amino acids; see specification as filed for
     detailed description of R-groups, substitutions and preferred
     embodiments
<220> FEATURE:
<223> OTHER INFORMATION: n-term may be acetylated
<220> FEATURE:
<223> OTHER INFORMATION: c-term may be amidatated

<400> SEQUENCE: 10

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Glu Gly Tyr Val Cys Val Glu Trp Ala Ala Cys Pro Thr
        35                  40                  45

Cys Arg Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
            85
```

<210> SEQ ID NO 11
<211> LENGTH: 85
<212> TYPE: PRT
<213> ORGANISM: Artificial Sequence
<220> FEATURE:
<223> OTHER INFORMATION: Description of Artificial Sequence: Synthetic
     formula peptide
<220> FEATURE:
<221> NAME/KEY: DISULFID
<222> LOCATION: (46)..(49)
<223> OTHER INFORMATION: this peptide may exhibit internal disulfide
     bonding
<220> FEATURE:
<221> NAME/KEY: DISULFID
<222> LOCATION: (40)
<223> OTHER INFORMATION: this peptide may exhibit dimerization at this
     residue
<220> FEATURE:
<221> NAME/KEY: MOD_RES
<222> LOCATION: (1)..(35)
<223> OTHER INFORMATION: Variable amino acid; this range may encompass
     0 to 35 amino acids with the proviso that total peptide length
     does not exceed 50 amino acids; see specification as filed for
     detailed description of R-groups, substitutions and preferred
     embodiments
<220> FEATURE:
<221> NAME/KEY: MOD_RES
<222> LOCATION: (51)..(85)
<223> OTHER INFORMATION: Variable amino acid; this range may encompass
     0 to 35 amino acids with the proviso that total peptide length
     does not exceed 50 amino acids; see specification as filed for
     detailed description of R-groups, substitutions and preferred
     embodiments
<220> FEATURE:
<223> OTHER INFORMATION: n-term may be acetylated
<220> FEATURE:
<223> OTHER INFORMATION: c-term may be amidatated

<400> SEQUENCE: 11

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Glu Gly Tyr Val Cys Val Glu Trp Ala Arg Cys Pro Thr
        35                  40                  45
```

Cys Lys Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 12
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acylated with aminohexanoic acid
<220> FEATURE:
<223> OTHER INFORMATION: c-term may be amidatated

<400> SEQUENCE: 12

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Glu Gly Tyr Val Cys Val Glu Trp Ala Arg Cys Pro Thr
            35                  40                  45

Cys Arg Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 13
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID

```
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 13

Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Glu Gly Tyr Val Cys Val Glu Phe Ala Arg Cys Pro Thr
            35                  40                  45

Cys Gly Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
             85

<210> SEQ ID NO 14
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
```

```
            0 to 35 amino acids with the proviso that total peptide length
            does not exceed 50 amino acids; see specification as filed for
            detailed description of R-groups, substitutions and preferred
            embodiments
<220> FEATURE:
<223> OTHER INFORMATION: n-term may be acetylated
<220> FEATURE:
<223> OTHER INFORMATION: c-term may be amidatated

<400> SEQUENCE: 14

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
                 20                  25                  30

Xaa Xaa Xaa Glu Gly Tyr Val Cys Val Glu Phe Ala Arg Cys Pro Thr
             35                  40                  45

Cys Arg Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa
             85

<210> SEQ ID NO 15
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 15

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
                 20                  25                  30

Xaa Xaa Xaa Glu Gly Tyr Val Cys Val Glu Trp Ala Arg Cys Pro Thr
             35                  40                  45
```

```
Cys Gly Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 16
<211> LENGTH: 85
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding as well as dimerization
<220> FEATURE:
<221> NAME/KEY: MOD_RES
<222> LOCATION: (1)..(35)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(85)
<223> OTHER INFORMATION: Variable amino acid; this range may encompass
      0 to 35 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 16

Xaa Xaa Xaa Xaa Xaa Xaa Xaa Xaa Xaa Xaa Xaa Xaa Xaa Xaa Xaa Xaa
1                   5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Glu Gly Tyr Val Lys Val Glu Trp Ala Arg Cys Pro Thr
        35                  40                  45

Cys Arg Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 17
<211> LENGTH: 86
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
```

```
<223> OTHER INFORMATION: this peptide may exhibit dimerization at this
      residue
<220> FEATURE:
<221> NAME/KEY: MOD_RES
<222> LOCATION: (1)..(36)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(86)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 17

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Gly Tyr Val Cys Val Glu Phe Ala Arg Cys Pro Thr
        35                  40                  45

Cys Gly Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa
            85

<210> SEQ ID NO 18
<211> LENGTH: 86
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (46)..(49)
<223> OTHER INFORMATION: this peptide may exhibit internal disulfide
      bonding
<220> FEATURE:
<221> NAME/KEY: DISULFID
<222> LOCATION: (40)
<223> OTHER INFORMATION: this peptide may exhibit dimerization at this
      residue
<220> FEATURE:
<221> NAME/KEY: MOD_RES
<222> LOCATION: (1)..(36)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(86)
<223> OTHER INFORMATION: Variable amino acid; this range may encompass
      0 to 36 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
```

```
<220> FEATURE:
<223> OTHER INFORMATION: c-term may be amidatated

<400> SEQUENCE: 18

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Gly Tyr Val Cys Val Glu Trp Ala Arg Cys Pro Thr
            35                  40                  45

Cys Arg Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa
                85

<210> SEQ ID NO 19
<211> LENGTH: 82
<212> TYPE: PRT
<213> ORGANISM: Artificial Sequence
<220> FEATURE:
<223> OTHER INFORMATION: Description of Artificial Sequence: Synthetic
      formula peptide
<220> FEATURE:
<221> NAME/KEY: DISULFID
<222> LOCATION: (36)..(47)
<223> OTHER INFORMATION: this peptide may exhibit internal disulfide
      bonding as well as dimerization
<220> FEATURE:
<221> NAME/KEY: MOD_RES
<222> LOCATION: (1)..(32)
<223> OTHER INFORMATION: Variable amino acid; this range may encompass
      0 to 32 amino acids with the proviso that total peptide length
      does not exceed 50 amino acids; see specification as filed for
      detailed description of R-groups, substitutions and preferred
      embodiments
<220> FEATURE:
<221> NAME/KEY: MOD_RES
<222> LOCATION: (51)..(82)
<223> OTHER INFORMATION: Variable amino acid; this range may encompass
      0 to 32 amino acids with the proviso that total peptide length
      does not exceed 50 amino acids; see specification as filed for
      detailed description of R-groups, substitutions and preferred
      embodiments
<220> FEATURE:
<223> OTHER INFORMATION: n-term may be acetylated
<220> FEATURE:
<223> OTHER INFORMATION: c-term may be amidatated

<400> SEQUENCE: 19

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Val Asp Glu Cys Trp Arg Ile Ile Ala Ser His Thr Trp Phe Cys Ala
            35                  40                  45

Glu Glu Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa
```